US010231655B2

(12) United States Patent
Wedekind et al.

(10) Patent No.: US 10,231,655 B2
(45) Date of Patent: Mar. 19, 2019

(54) CONTINUOUS ANALYTE MONITORING SYSTEM POWER CONSERVATION

(71) Applicant: DexCom, Inc., San Diego, CA (US)

(72) Inventors: Jeffrey R. Wedekind, San Diego, CA (US); Douglas William Burnette, San Diego, CA (US); Mark Dervaes, Carlsbad, CA (US); Jose Hector Hernandez-Rosas, San Diego, CA (US); Zebediah L. McDaniel, San Diego, CA (US); Pauline T. Lieu, San Diego, CA (US); Minda McDorman Grucela, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 35 days.

(21) Appl. No.: 15/369,610

(22) Filed: Dec. 5, 2016

(65) Prior Publication Data

US 2017/0172473 A1    Jun. 22, 2017

Related U.S. Application Data

(63) Continuation of application No. 15/369,336, filed on Dec. 5, 2016.

(60) Provisional application No. 62/270,485, filed on Dec. 21, 2015.

(51) Int. Cl.
| | | |
|---|---|---|
| G02B 21/00 | (2006.01) | |
| A61B 5/145 | (2006.01) | |
| A61B 5/00 | (2006.01) | |
| G06F 19/00 | (2018.01) | |

(52) U.S. Cl.
CPC .......... *A61B 5/14532* (2013.01); *A61B 5/002* (2013.01); *A61B 5/0004* (2013.01); *A61B 5/0031* (2013.01); *A61B 5/14503* (2013.01); *A61B 5/742* (2013.01); *G06F 19/00* (2013.01); *G06F 19/30* (2013.01); *A61B 2560/0209* (2013.01); *A61B 2560/0242* (2013.01); *A61B 2562/08* (2013.01); *A61B 2562/164* (2013.01)

(58) Field of Classification Search
CPC .......................... A61B 5/14532; A61B 5/0002
USPC ........... 340/540, 541, 636.1, 636.12, 636.19, 340/693.1, 384.5; 320/132
See application file for complete search history.

(56) References Cited

U.S. PATENT DOCUMENTS

| | | | | |
|---|---|---|---|---|
| 6,957,091 B1 * | 10/2005 | Ptasinski | ............ | G01R 31/3613 |
| | | | | 455/572 |
| 7,430,675 B2 | 9/2008 | Lee | | |
| 8,461,985 B2 * | 6/2013 | Fennell | ................ | A61B 5/0002 |
| | | | | 340/540 |
| 8,868,151 B2 | 10/2014 | Telson et al. | | |

(Continued)

*Primary Examiner* — Tai T Nguyen
(74) *Attorney, Agent, or Firm* — Knobbe Martens Olson & Bear, LLP

(57) ABSTRACT

Disclosed are devices, systems and methods for power management in an electronics unit of a sensor device, e.g., such as in a continuous analyte sensor system. In some example embodiments, there is provided a method that includes monitoring, by a controller of a sensor electronics module, counts associated with signals received from a sensor device for a first period of time. The method also includes comparing a number of received counts with one or more benchmarked count thresholds, and determining whether to initiate an operational mode of the sensor electronics module based on the comparison. Related systems, methods, and articles of manufacture are also described.

6 Claims, 15 Drawing Sheets

(56) References Cited

U.S. PATENT DOCUMENTS

| | | | |
|---|---|---|---|
| 8,929,995 B2 | 1/2015 | Stancer et al. | |
| 8,993,331 B2 | 3/2015 | Nekoomaram et al. | |
| 9,144,204 B2 | 9/2015 | Redmond et al. | |
| 9,196,139 B2 | 11/2015 | Gutierrez et al. | |
| 9,566,450 B2 | 2/2017 | Joglekar et al. | |
| 9,830,670 B2 | 11/2017 | Fadell | |
| 2004/0017180 A1* | 1/2004 | Cook | G01R 31/3648 320/132 |
| 2010/0207585 A1 | 8/2010 | DuValsaint et al. | |
| 2013/0231541 A1 | 9/2013 | Hayter et al. | |
| 2015/0077127 A1* | 3/2015 | Fu | G06F 1/3212 324/428 |
| 2015/0164391 A1 | 6/2015 | Hernandez-Rosas et al. | |
| 2015/0208971 A1 | 7/2015 | Hayter et al. | |
| 2015/0308960 A1 | 10/2015 | Shih | |
| 2016/0073351 A1* | 3/2016 | Cardozo | H04W 52/0258 455/574 |

* cited by examiner

CONTINUOUS ANALYTE MONITORING SYSTEM POWER CONSERVATION

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. appl. Ser. No. 15/369,336, filed Dec. 5, 2016, which claims the benefit of U.S. Provisional Appl. No. 62/270,485, filed on Dec. 21, 2015. Each of the aforementioned applications is incorporated by reference herein in its entirety, and each is hereby expressly made a part of this specification.

FIELD

Various embodiments relate generally to continuous monitoring of analyte values received from an analyte sensor system, and in particular, to power conservation in the analyte sensor system.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic person will normally only measure his or her glucose level two to four times per day. Unfortunately, these time intervals are spread so far apart that the diabetic person will likely find out too late, sometimes incurring dangerous side effects, of a hyperglycemic or hypoglycemic condition. In fact, it is not only unlikely that a diabetic person will take a timely SMBG value, but it is also unlikely that the diabetic will know if his or her blood glucose value is going up (higher) or down (lower) utilizing conventional monitoring systems and methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In some aspects of the disclosed technology, a computer-implemented method for managing power modes of an electronic device includes monitoring, by a controller of a sensor electronics module, counts associated with signals received from a sensor device for a first period of time; comparing a number of received counts with one or more benchmarked count thresholds; and, determining whether to initiate an operational mode of the sensor electronics module based on the comparison. In some implementations, The computer-implemented method further includes performing the initiation of the operational mode of the sensor electronics module based on a determination that the number of received counts meets or exceeds a first benchmarked count threshold of the one or more benchmarked count thresholds for the first period of time. In some implementations, the computer-implemented method further includes, prior to the initiating of the operational mode of the sensor electronics module, monitoring counts for a second period of time; determining whether another number of received counts from the second period of time exceeds a second benchmarked count threshold of the one or more benchmarked thresholds for the second period of time; and wherein the performance of the initiation of the operational mode is further based upon a determination the other number of received counts from the second period of time meets or exceeds the second benchmarked count threshold for the second period of time. In some implementations, the second benchmarked count threshold is less that the first benchmarked count threshold and the second period of time is less that the first period of time. In some implementations, the number of counts for the second period of time divided by the duration of the second period of time is equal to the number of counts for the first period of time divided by the duration of the first period of time. In some implementations, the monitoring the counts for the second period of time includes monitoring the counts over a plurality of intervals comprising the second period of time. In some implementations, the plurality of intervals includes consecutive intervals.

In some aspects of the disclosed technology, a computer-implemented method for managing power modes of an electronic device includes monitoring, by a controller of a sensor electronics module, counts associated with signals received from a sensor device for one or more periods of time; comparing a number of received counts with one or more benchmarked count thresholds for a plurality of time intervals; and distinguishing between a wakeup event of the sensor electronics module and an anomalous event based on the comparison. In some implementations, the computer-implemented method further includes determining that the anomalous event has occurred due to an electrostatic discharge when the received counts is lower than the benchmarked count threshold. In some implementations, the computer-implemented method further includes determining that the anomalous event has occurred due to an electrostatic discharge when the received counts are higher or lower for only one time interval of the plurality of consecutive time intervals.

In some aspects of the disclosed technology, an activation circuit, includes a battery; a load switch circuit operatively connected to one or more components of a sensor electronics module, the sensor electronics module receiving sensor information from a continuous analyte sensor, the load switch circuit adapted to connect the battery to or disconnect the battery from the one or more components of a sensor electronics module; and a control circuit controlling the connection of the battery to and disconnection of the battery from the one or more components of a sensor electronics module.

In some aspects of the disclosed technology, a circuit includes a timer operatively connected to one or more components of a sensor electronics module, the sensor electronics module to receive sensor information from a continuous analyte sensor, the timer being adapted to receive periodic reset signals to prevent timing out of the timer; and a low-frequency oscillator implemented externally to the one or more components of the sensor electronics module, the low-frequency oscillator being adapted to transmit the periodic reset signals to the timer and transmit a wake signal to the one or more components of the sensor electronics module upon detecting that the one or more components of the sensor electronics module require waking.

In some aspects of the disclosed technology, an apparatus includes an analyte sensor; a sensor electronics module operatively connected to the analyte sensor and adapted to receive analyte sensor data from the analyte sensor; and an authentication circuit authenticating one or more batteries installed in the sensor electronics module.

In some aspects of the disclosed technology, an apparatus includes an analyte sensor; a sensor electronics module operatively connected to the analyte sensor and adapted to receive analyte sensor data from the analyte sensor; and a temperature sensor adapted to determine at least one of an operating temperature of the sensor electronics module and an ambient temperature about the sensor electronics module.

In some aspects of the disclosed technology, a computer-implemented method for estimating battery life includes measuring a current power level of a battery powering an analyte sensor system; predicting a remaining useful life of the battery based upon the measured current power level of the battery and an assumed usage of the analyte sensor system; determining whether the predicted remaining useful life of the battery is less than a predetermined time; and adjusting at least one of advertising and communication parameters for effectuating communications between the analyte sensor system and one or more display devices.

Any of the features of aspects specified herein are applicable to all other aspects and embodiments identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can be performed by a system or apparatus of another aspect, and any aspect or of a system can be configured to perform a method of another aspect.

BRIEF DESCRIPTION OF THE DRAWINGS

Various embodiments are described in detail with reference to the accompanying figures. The drawings are provided for purposes of illustration only and merely depict typical or example embodiments. These drawings are provided to facilitate the reader's understanding of the systems and methods described herein, and shall not be considered limiting of the breadth, scope, or applicability of the various embodiments.

DETAILED DESCRIPTION

Figure 1:
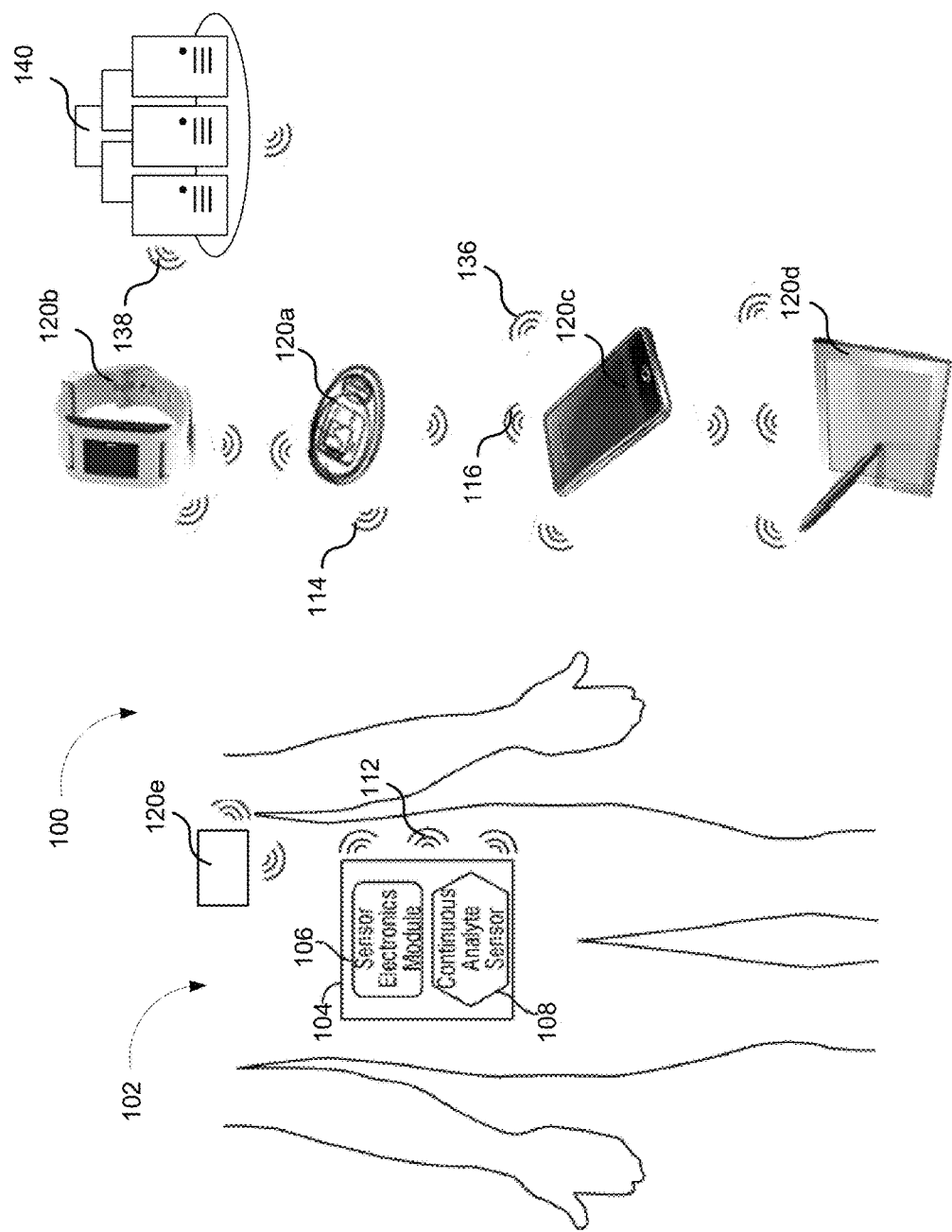
FIG. 1 is a diagram illustrating certain embodiments of an example continuous analyte sensor system communicating with at least one display device in accordance with various technologies described in the present disclosure.

The following description illustrates some example embodiments of the disclosed technology or technologies in detail. Those of skill in the art will recognize that there are numerous variations and modifications of the disclosed embodiments that are encompassed by its scope. Accordingly, the description of a certain example embodiment should not be deemed to limit the scope of the present disclosure.

Overview

In some embodiments, a system is provided for continuous measurement of an analyte in a host that includes: a continuous analyte sensor configured to continuously measure a concentration of the analyte in the host; and a sensor electronics module physically connected to the continuous analyte sensor to receive the analyte concentration measurements and communicate them to display devices. In particular, the sensor electronics module includes electronics configured to process a data stream associated with an analyte concentration measured by the continuous analyte sensor in order to generate sensor information that includes raw sensor data, transformed sensor data, and/or any other sensor data or data derived therefrom, e.g., predictive or trend data. The sensor electronics module may further be configured to generate sensor information that is customized for respective display devices, such that different display devices may receive different sensor information for presentation to the host, a host care taker, etc. Further still, the sensor electronics module includes one or more communication modules, such as wireless radio transmitters for transmitting the sensor information to the display devices.

As can be appreciated, the nature of continual analyte measurement, as well as a desired form factor for the sensor electronics module would be well-served by a power efficient design. Thus, various aspects of the sensor electronics module are optimized in accordance with various embodiments so as to save power/maximize battery life therein.

In some aspects of the disclosed technology, a computer-implemented method for managing power modes of an electronic device includes monitoring, by a controller of a sensor electronics module, counts associated with signals received from a sensor device for a first period of time; comparing a number of received counts with a benchmarked count threshold; and upon a determination that the number of received counts meets or exceeds the benchmarked count threshold, initiating an operational mode of the sensor electronics module.

Implementations of the computer-implemented method can include one or more of the following example features. For example, in some implementations of the computer-implemented method, the sensor device includes a continuous analyte sensor, and when the sensor electronics module is in the operational mode, in which the computer-implemented method further includes transmitting estimated analyte value data to one or more display devices. The estimated analyte value data can include estimated glucose values. In some implementations, the signals include sensor information from which the transmitted estimated analyte value data is derived. In some implementations, the continuous analyte monitoring sensor includes a continuous glucose monitoring sensor. In some implementations, the computer-implemented method further includes receiving a wake event, in which the wake event comprises a signal received by at least the controller of the sensor electronics module from a wake source component implemented between the controller and the sensor device operatively connected to the sensor electronics module. In some implementations, the computer-implemented method further includes, prior to the initiating an operational mode of the sensor electronics module, monitoring counts for a second period of time; determining whether the number of received counts from the second period of time exceeds a second benchmarked count threshold for the second period of time; and upon a determination the number of received counts from the second period of time meets or exceeds the second benchmarked count threshold for the second period of time, initiating the operational mode of the sensor electronics module. In some implementations, the second benchmarked count threshold is less that the first benchmarked count threshold and the second period of time is less that the first period of time. In some implementations, the number of counts for the second period of time divided by the duration of the second period of time is equal to the number of counts for the first period of time divided by the duration of the first period of time. In some implementations, the monitoring the counts for the second period of time includes monitoring the counts over a plurality of intervals comprising the second period of time. In some implementations, the plurality of intervals includes consecutive intervals.

In some aspects of the disclosed technology, an activation circuit, includes a battery; a load switch circuit operatively connected to one or more components of a sensor electronics module, the sensor electronics module receiving sensor information from a continuous analyte sensor, the load switch circuit adapted to connect the battery to or disconnect the battery from the one or more components of a sensor electronics module; and a control circuit controlling the connection of the battery to and disconnection of the battery from the one or more components of a sensor electronics module.

Implementations of the activation circuit can include one or more of the following example features. For example, in some implementations of the activation circuit, the disconnection of the battery from the one or more components of the sensor electronics module comprises prevention of current flow from the battery to the one or more components of the sensor electronics module. In some implementations, the disconnection of the battery from the one or more components of the sensor electronics module comprises a default storage state. In some implementations, the default storage state is entered subsequent to installation of the battery on a circuit assembly and prior to testing of the circuit assembly. In some implementations, the control circuit is operable to receive an activation signal to connect the battery to the one or more components of the sensor electronics module. In some implementations, the control circuit is operable to produce a subsequent activation signal upon receipt of the activation signal to be transmitted to the load switch circuit instructing the load switch circuit to enable current flow from the battery to the one or more components of the sensor electronics module. In some implementations, the control circuit is operable to receive an activation signal to connect the battery to the one or more components of the sensor electronics module subsequent to installation of the battery on a circuit assembly and substantially immediately prior to final encapsulation of the circuit assembly within a housing. In some implementations, the one or more components of the sensor electronics module comprise at least an application-specific integrated circuit.

In some aspects of the disclosed technology, a circuit includes a timer operatively connected to one or more components of a sensor electronics module, the sensor electronics module to receive sensor information from a continuous analyte sensor, the time being adapted to receive periodic reset signals to prevent timing out of the timer; and a resistor-capacitor (RC) oscillator implemented externally to the one or more components of the sensor electronics module, the RC oscillator being adapted to transmit the periodic reset signals to the timer and transmit a wake signal to the one or more components of the sensor electronics module upon detecting that the one or more components of the sensor electronics module require waking.

Implementations of the circuit can include one or more of the following example features. For example, in some implementations of the circuit, the timer comprises a watchdog timer. In some implementations, the RC oscillator comprises a very low power low-frequency oscillator. In some implementations, the RC oscillator comprises a general-purpose RC oscillator re-configured for operation with the timer. In some implementations, the one or more sensor electronics modules revert to one of a low power or no power state upon receipt of the periodic reset signals. In some implementations, upon receiving the wake signal, the one or more components of the sensor electronics module wake up and transmit estimated analyte value data to one or more display devices.

In some aspects of the disclosed technology, an apparatus includes an analyte sensor; a sensor electronics module operatively connected to the analyte sensor and adapted to receive analyte sensor data from the analyte sensor; and an authentication circuit authenticating one or more batteries installed in the sensor electronics module.

Implementations of the apparatus can include one or more of the following example features. For example, in some implementations of the apparatus, the authentication circuit is operable to instruct a processor of the sensor electronics module to read authentication data associated with the one or more batteries. In some implementations, the authentication data comprises at least one of an identification code associated with each of the one or more batteries and a cyclic redundancy check value associated with each of the one or more batteries. In some implementations, the one or more batteries temporarily power the sensor electronics module during authentication of the one or more batteries by the authentication circuit. In some implementations, operation of the sensor electronics module is inhibited upon a failed authentication regarding any of the one or more batteries. In some implementations, an operational mode of the sensor electronics module is selected depending on the authentication of the one or more batteries. In some implementations, the apparatus further includes a sensor adapted to detect high current conditions within the sensor electronics module.

In some aspects of the disclosed technology, an apparatus includes an analyte sensor; a sensor electronics module operatively connected to the analyte sensor and adapted to receive analyte sensor data from the analyte sensor; and a temperature sensor adapted to determine at least one of an operating temperature of the sensor electronics module and an ambient temperature about the sensor electronics module.

Implementations of the apparatus can include one or more of the following example features. For example, in some implementations of the apparatus, the apparatus is operable to adjust an estimation of remaining battery life of at least one battery powering the sensor electronics module based upon one of a temperature-battery power skew table and a temperature-battery power skew correction mechanism.

In some aspects of the disclosed technology, a computer-implemented method for estimating battery life includes measuring a current power level of a battery powering an analyte sensor system; predicting a remaining useful life of the battery based upon the measured current power level of the battery and an assumed usage of the analyte sensor system; determining whether the predicted remaining useful life of the battery is less than a predetermined time; and adjusting at least one of advertising and communication parameters for effectuating communications between the analyte sensor system and one or more display devices.

Implementations of the computer-implemented method can include one or more of the following example features. For example, in some implementations of the computer-implemented method, the computer-implemented method further includes transmitting a notification to at least one of the one or more display devices upon a determination that the predicted remaining useful life of the battery is less than the predetermined time. In some implementations, the computer-implemented method further includes delaying the communications between the analyte sensor system and the one or more display devices upon a determination that a current trend of analyte measurements received by the analyte sensor system is indicative that a user of the analyte sensor system is in a clinically safe zone. In some implementations, the computer-implemented method further includes at least one of transmitting an alarm indicating that the battery requires replacement upon a determination that a current trend of analyte measurements received by the analyte sensor system is indicative that a user of the analyte sensor system is in a clinically unsafe zone and upon a determination that the predicted remaining useful life of the battery is less than the predetermined time. In some implementations, the computer-implemented method further includes handing off at least one of advertising for communications between the analyte sensor system and the one or more display devices and forwarding of analyte sensor information to the one or more display devices to one of the one or more display devices upon a determination that a current trend of analyte measurements received by the analyte sensor system is indicative that a user of the analyte sensor system is in a clinically unsafe zone and upon a determination that the predicted remaining useful life of the battery is less than the predetermined time.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, and/or reaction products. In some implementations, the analyte for measurement by the methods or devices is glucose. However, other analytes are contemplated as well, including but not limited to: acarboxyprothrombin; acetoacetic acid; acetone; Acetyl CoA; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; ketone bodies; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, isoprene (2-methyl-1,3-butadiene), Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, Flavivirus (for example deer tick virus, dengue fever virus, Powassan virus, West Nile virus, yellow fever virus, or Zika virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. The analyte can be naturally present in the biological fluid, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon, ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3 MT), 3,4-Dihydroxyphenylacetic acid (DOPAC), Homovanillic acid (HVA), 5-Hydroxytryptamine (5 HT), and 5-Hydroxyindoleacetic acid (FHIAA), and intermediaries in the Citric Acid Cycle.

In general, and as alluded to above, a plurality of display devices (e.g., a custom analyte monitoring device, a mobile phone, a tablet, a smart watch, a reference analyte monitor, a medicament delivery device, a medical device and/or a personal computer) may be configured to wirelessly communicate with the sensor electronics module. The one or more display devices can be configured to display at least some of the sensor information wirelessly communicated by the sensor electronics module. The sensor information may include, for example, sensor data, such as raw data and/or transformed sensor data, such as analyte concentration values, rate of change information, trend information, alert information, sensor diagnostic information, calibration information, non-visual information such as temperature readings, sound, etc.

The terms "raw data," "raw data stream", "raw data signal", "data signal", and "data stream" as used herein can refer without limitation to an analog or digital signal from the continuous analyte sensor related to a measured analyte. For example, a raw data stream provided by the continuous analyte sensor to the sensor electronics module may be digital data in "counts" converted by an A/D converter from an analog signal (for example, voltage or current) representative of an analyte concentration, which can include a plurality of time spaced data points from a substantially continuous analyte sensor, each of which comprises individual measurements taken at time intervals ranging from fractions of a second up to, for example, one, two, or five minutes or longer. In some embodiments, the raw data/counts may be representative of sensor information that has been integrated or averaged over a time period (e.g., five minutes). Moreover, the term "count" can refer to a unit of measurement of a digital signal. For example, a raw data stream or raw data signal measured in counts is related to a voltage (for example, converted by an A/D converter), which is directly related to current from the working electrode.

In some embodiments, the sensor electronics module may be configured to search for and/or attempt to wirelessly communicate with a display device. In some embodiments, the search for and/or attempted wireless communication with the display device can occur in a predetermined and/or programmable order (e.g., grading and/or escalating). For example, if an attempt at communicating with and/or alarming a first display device fails, this failure triggers an attempt to communicate with and/or alarm a second display device, and so on. It should be noted that the sensor electronics module is not necessarily tied to a single display device. Rather the sensor electronics module is configured to communicate with a plurality of different display devices directly, systematically, simultaneously (e.g., via broadcasting), regularly, periodically, randomly, on-demand, in response to a query, based on alerts or alarms, and/or the like.

Depending on the embodiment, the sensor electronics module receives sensor information from the continuous analyte sensor. This sensor information may be raw data which the display device receives and processes, e.g., in accordance with one or more algorithms, for generating and/or displaying estimated analyte values. In the context of continuous glucose monitoring, the estimated analyte values may be estimated glucose value (EGV) data. For example, some display devices may comprise software including display instructions (software programming comprising instructions configured to display the sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the sensor information via a downloadable program (for example, a downloadable Java Script via the internet), such that any display device that supports downloading of a program (for example, any display device that supports Java applets) can be configured to display displayable sensor information (e.g., mobile phones, tablets, PDAs, PCs and the like).

In other embodiments, the processing of the raw data may be performed at the sensor electronics module. That is, the requisite algorithms, software, and/or other processing functionality for transforming the raw data into estimated analyte value data may be implemented at the sensor electronics module rather than at the display device. Transforming the raw data at the sensor electronics module may avoid the possibility for inconsistent estimated analyte value data, e.g., due to inconsistent calibration between two or more display devices. Moreover, implementing this functionality at the sensor electronics module may discourage third party display device/medicament delivery device providers from tampering or otherwise altering the processing algorithms and software.

In some embodiments, certain display devices may be in direct wireless communication with the sensor electronics module, although intermediate network hardware, firmware, and/or software can be included within the direct wireless communication. In some embodiments, a repeater (e.g., a Bluetooth repeater) can be used to re-transmit the transmitted sensor information to a location farther away than the immediate range of the telemetry module of the sensor electronics module. In some embodiments, a receiver (e.g., Bluetooth receiver) can be used to re-transmit the transmitted sensor information to a display device, e.g., a TV screen, possibly in a different format, such as in a text message.

In some embodiments, one or more display devices are configured to query the sensor electronics module for sensor information, where the display device requests sensor information from the sensor electronics module in an "on-demand" fashion, for example, in response to a query. In some embodiments, the sensor electronics module is configured for periodic, systematic, regular, or irregular or aperiodic transmission of sensor information to one or more display devices (for example, every one, two, five, or ten minutes or more). In some embodiments, the sensor electronics module is configured to transmit data packages associated with a triggered alert (e.g., triggered by one or more alert conditions). However, any combination of the above described statuses of data transmission can be implemented with any combination of a paired sensor electronics module and display device(s). For example, one or more display devices can be configured for querying a sensor electronics module database and for receiving alarm information triggered by one or more alarm conditions being met. Additionally, the sensor electronics module can be configured to transmit sensor information to one or more display devices (the same or different display devices as described in the previous example), where the display devices function differently with regard to how they obtain sensor information.

In some embodiments, as described in more detail below, a display device is configured to query data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

Example Configurations of a Continuous Analyte Monitoring System

FIG. 1 is a diagram depicting an example continuous analyte monitoring system 100 including an analyte sensor system 104 operatively connected to a host 102 and a plurality of display devices 120a-e according to certain aspects of the present disclosure. It should be noted that display device 120e alternatively or in addition to being a display device, may be a medicament delivery device that can act cooperatively with the analyte sensor system 104 to deliver medicaments to host 102. The analyte sensor system 104 may include a sensor electronics module 106 and a continuous analyte sensor 108 associated with the sensor electronics module 106. The sensor electronics module 106 may be in direct wireless communication with one or more of the plurality of the display devices 120a-e via wireless communications signals. As will be discussed in greater detail below, display devices 120a-e may also communicate amongst each other and/or through each other to analyte sensor system 104. For ease of reference, wireless communications signals from analyte sensor system 104 to display devices 120a-e can be referred to as "uplink" signals 112. Wireless communications signals from, e.g., display devices 120a-e to analyte sensor system 104 can be referred to as "downlink" signals 114. Wireless communication signals between two or more of display devices 120a-e may be referred to as "crosslink" signals 116. Additionally, wireless communication signals may include data transmitted by one or more of display devices 120a-d via "long-range" uplink signals 136 (e.g., cellular signals) to one or more remote servers 140 or network entities, such as cloud-based servers or databases, and receive long-range downlink signals 138 transmitted by remote servers 140.

The sensor electronics module 106 includes sensor electronics that are configured to process sensor information and generate transformed sensor information. In certain embodiments, the sensor electronics module 106 includes electronic circuitry associated with measuring and processing data from continuous analyte sensor 108, including prospective algorithms associated with processing and calibration of the continuous analyte sensor data. The sensor electronics module 106 can be integral with (non-releasably attached to) or releasably attachable to the continuous analyte sensor 108 achieving a physical connection therebetween. The sensor electronics module 106 may include hardware, firmware, and/or software that enables analyte level measurement. For example, the sensor electronics module 106 can include a potentiostat, a power source for providing power to continuous analyte sensor 108, other components useful for signal processing and data storage, and a telemetry module for transmitting data from itself to one or more display devices 120a-e. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Display devices 120a-e are configured for displaying, alarming, and/or basing medicament delivery on the sensor information that has been transmitted by the sensor electronics module 106 (e.g., in a customized data package that is transmitted to one or more of display devices 120a-e based on their respective preferences). Each of the display devices 120a-e can include a display such as a touchscreen display for displaying sensor information to a user (most often host 102 or a care taker/medical professional) and/or receiving inputs from the user. In some embodiments, the display devices 120a-e may include other types of user interfaces such as a voice user interface instead of or in addition to a touchscreen display for communicating sensor information to the user of the display device 120a-e and/or receiving user inputs. In some embodiments, one, some or all of the display devices 120a-e are configured to display or otherwise communicate the sensor information as it is communicated from the sensor electronics module 106 (e.g., in a data package that is transmitted to respective display devices 120a-e), without any additional prospective processing required for calibration and real-time display of the sensor information.

In the embodiment of FIG. 1, one of the plurality of display devices 120a-e may be a custom display device 120a specially designed for displaying certain types of displayable sensor information associated with analyte values received from the sensor electronics module 106 (e.g., a numerical value and an arrow, in some embodiments). In some embodiments, one of the plurality of display devices 120a-e may be a handheld device 120c, such as a mobile phone based on the Android or iOS operating system, a palm-top computer and the like, where handheld device 120c may have a relatively larger display and be configured to display a graphical representation of the continuous sensor data (e.g., including current and historic data). Other display devices can include other hand-held devices, such as a tablet 120d, a smart watch 120b, a medicament delivery device 120e, a blood glucose meter, and/or a desktop or laptop computer.

As alluded to above, because the different display devices 120a-e provide different user interfaces, content of the data packages (e.g., amount, format, and/or type of data to be displayed, alarms, and the like) can be customized (e.g., programmed differently by the manufacture and/or by an end user) for each particular display device and/or display device type. Accordingly, in the embodiment of FIG. 1, one or more of display devices 120a-e can be in direct or indirect wireless communication with the sensor electronics module 106 to enable a plurality of different types and/or levels of display and/or functionality associated with the sensor information, which is described in more detail elsewhere herein.

Continuous Analyte Sensor

Continuous analyte sensor 108 of FIG. 1 may be, for example a subcutaneous, transdermal (e.g., transcutaneous), or intravascular device. In some embodiments, continuous analyte sensor 108 can analyze a plurality of intermittent blood samples, although continuous analyte sensor 108 can be configured to use any method of analyte-measurement, including enzymatic, chemical, physical, electrochemical, spectrophotometric, polarimetric, calorimetric, iontophoretic, radiometric, immunochemical, and the like.

Continuous analyte sensor 108 can use any known method, including invasive, minimally invasive, and non-invasive sensing techniques (e.g., fluorescent monitoring), to provide a data stream indicative of the concentration of a measured analyte in host 102. In some embodiments, this data stream is typically a raw data signal, which is converted into a calibrated and/or filtered data stream that is used to provide a useful value of the measured analyte to a user, such as host 102 or a caretaker (e.g., a parent, a relative, a guardian, a teacher, a doctor, a nurse, or any other individual that has an interest in the well-being of host 102). It should be understood that the devices and methods described herein can be applied to any device capable of detecting a concentration of an analyte and providing an output signal that represents the concentration of the analyte.

In some embodiments, continuous analyte sensor 108 may be capable of measuring a concentration of glucose in host 102, one of which is described below as utilizing an implantable continuous glucose sensor. For example, continuous analyte sensor 108 may be an implantable glucose sensor, such as described with reference to U.S. Pat. No. 6,001,067 and U.S. Patent Publication No. US-2005-0027463-A1. In another embodiment, continuous analyte sensor 108 may be a transcutaneous glucose sensor, such as described with reference to U.S. Patent Publication No. US-2006-0020187-A1. In still other embodiments, continuous analyte sensor 108 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, co-pending U.S. Patent Publication No. US-2008-0108942-A1 filed on Mar. 26, 2007, and co-pending U.S. Patent Application No. US-2007-0197890-A1 filed on Feb. 14, 2007. In one alternative embodiment, continuous analyte sensor 108 comprises a transcutaneous sensor such as described in U.S. Pat. No. 6,565,509 to Say et al., for example. In another alternative embodiment, continuous analyte sensor 108 comprises a subcutaneous sensor such as described with reference to U.S. Pat. No. 6,579,690 to Bonnecaze et al. or U.S. Pat. No. 6,484,046 to Say et al., for example. In another alternative embodiment, continuous analyte sensor 108 comprises a refillable subcutaneous sensor such as described with reference to U.S. Pat. No. 6,512,939 to Colvin et al., for example. In another alternative embodiment, continuous analyte sensor 108 comprises an intravascular sensor such as described with reference to U.S. Pat. No. 6,477,395 to Schulman et al., for example. In another alternative embodiment, continuous analyte sensor 108 comprises an intravascular sensor such as described with reference to U.S. Pat. No. 6,424,847 to Mastrototaro et al., for example.

Sensor Electronics Module

Figure 2A:
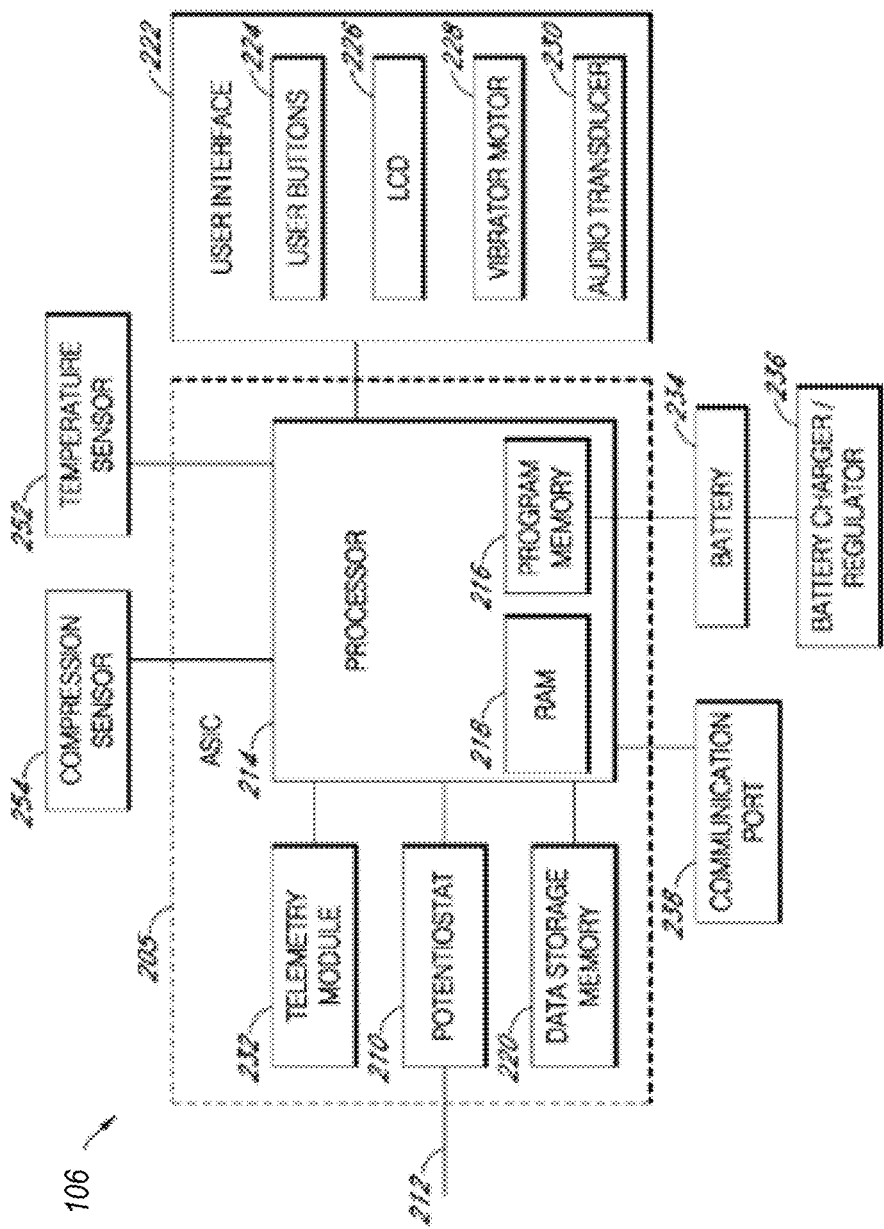
FIG. 2A is a block diagram of an example sensor electronics module of the example continuous analyte sensor system of FIG. 1.

FIG. 2A is a block diagram illustrating embodiments of the sensor electronics module 106 (FIG. 1). The sensor electronics module 12 can include an application-specific integrated circuit (ASIC) 205, a user interface 222, compression sensor 254 and temperature sensor 252. ASIC 205 can also be coupled to a communication port 238 and a battery 234. Although FIG. 2A shows an ASIC 205 that includes much of the electronic circuitry, the ASIC 205 may be replaced with one or more of any suitable logic device, such as field programmable gate arrays (FPGA), microprocessors, analog circuitry, or other digital and/or analog circuitry. Further, ASIC 205 can include one or more additional features of sensor electronics module 106 discussed elsewhere herein, or one or more features illustrated in FIG. 2A as being part of the ASIC—such as telemetry module 232, potentiostat 210, data storage memory 220—can be separate from the ASIC.

In this embodiment, a potentiostat 210 (one example of an analog front end (AFE)) is coupled to continuous analyte sensor 108 via data line 212, for example, in order to receive sensor information obtained/measured by continuous analyte sensor 108. In some embodiments, the potentiostat 210 provides a voltage to continuous analyte sensor 108 via data line 212 in order to bias continuous analyte sensor 108 to enable measurement of a current value indicative of the analyte concentration in the host (also referred to as the analog portion). The potentiostat 210 can have one channel or multiple channels (and a corresponding one or multiple data lines 212), depending on the number of working electrodes, for example. In some embodiments, the potentiostat 210 includes a resistor (not shown) that translates current into voltage. In some embodiments, a current to frequency converter is provided that is configured to continuously integrate the measured current, for example, using a charge counting device. In some embodiments, an A/D converter digitizes the analog signal into "counts" (previously described) for processing. Accordingly, the resulting raw data stream in counts can be directly related to the current measured by the potentiostat 210.

A processor 214 controls the processing of the sensor electronics module 106. In some embodiments, the processor 214 is formed as part of a custom chip, such as an ASIC, however a computer system other than an ASIC can be used to process data as described herein, for example a microprocessor can be used for some or all of the sensor electronics module processing. Processor 214 typically provides a program memory 216, which provides semi-permanent storage of data, for example, storing data such as sensor identifier (ID) and programming to process data streams (for example, filtering, calibration, fail-safe checking, and the like). Processor 214 can additionally be used for the cache memory of continuous analyte monitoring system 100, for example for temporarily storing recent sensor data. In some embodiments, processor 214 comprises memory storage components such as ROM, RAM, dynamic-RAM, static-RAM, non-static RAM, EEPROM, rewritable ROMs, flash memory, and the like. In one embodiment, RAM 218 can be used for the continuous analyte monitoring system 100's cache memory, for example for temporarily storing recent sensor information.

In some embodiments, processor 214 comprises a digital filter, for example, an infinite or finite impulse response (IIR or FIR) filter, configured to smooth the raw data stream from the A/D converter. Generally, digital filters are programmed to filter data sampled at a predetermined time interval (also referred to as a sample rate). In some embodiments, such as when the potentiostat 210 is configured to measure the analyte at discrete time intervals, these time intervals determine the sample rate of the digital filter. In some alternative embodiments, when potentiostat 210 is configured to continuously measure an analyte, for example, using a current-to-frequency converter, processor 214 can be programmed to request a digital value from an integrator at a predetermined time interval, also referred to as the acquisition time. In these alternative embodiments, the values obtained by the processor 214 can be averaged over the acquisition time due the continuity of the current measurement. Accordingly, the acquisition time determines the sample rate of the digital filter.

In an embodiment, the processor 214 may be further configured to generate data packages for transmission to one or more display devices. Furthermore, processor 214 may generate data packets for transmission to these outside sources, e.g., via telemetry. As discussed above, the data packages may be customizable for each display device 120*a-e*, for example, and may include any available data, such as sensor information having customized sensor data and/or transformed sensor data, sensor/sensor electronics module ID code, raw data, filtered data, calibrated data, rate of change information, trend information, error detection or correction, and/or the like.

A data storage memory 220 is operably connected to processor 214 and is configured to store a variety of sensor information. In some embodiments, the data storage memory stores, for example, 1, 5, 9, 14, 15, 20, 30 or more days of continuous analyte sensor data. In some embodiments, the data storage memory 220 stores sensor information such as raw sensor data (one or more raw analyte concentration values), calibrated data, filtered data, transformed sensor data, and/or any other displayable sensor information. Although separate data storage memory 220 and program memory 216 are shown in FIG. 2A, one skilled in the art appreciates a variety of configurations, including one or multiple memories that provide the necessary storage space to support sensor electronic module 106 data processing and storage requirements.

A telemetry module 232 is operably connected to the processor module 214 and provides the hardware, firmware, and/or software that enable wireless communication between the sensor electronics module 106 and one or more display devices 120*a-e*. A variety of wireless communication technologies that can be implemented in the telemetry module 232 include radio frequency (RF), infrared (IR), Bluetooth®, Bluetooth Low Energy (BLE), spread spectrum communication, frequency hopping communication, Zig-Bee, IEEE 802.11/802.16, wireless (e.g., cellular) telecommunication, paging network communication, magnetic induction, satellite data communication, GPRS, ANT, and/or the like. In one preferred embodiment, the telemetry module comprises a Bluetooth chip. In some embodiments, Bluetooth technology is implemented in a combination of the telemetry module 232 and processor 214.

A battery 234 is operatively connected to the processor 214 (and possibly other components of the sensor electronics module 106) and provides the necessary power for the sensor electronics module 106. In some embodiments, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments battery 234 is rechargeable. In some embodiments, a plurality of batteries can be used to power the system. In some embodiments, battery 234 may be a custom battery having one or more of a customized size, shape, and/or capacity optimized for use in sensor electronics module 106, including reduced capacity in cases where sensor electronics module 106 has lower energy requirements.

In some implementations, flexible electronics or flex circuit technology may be used to attach or incorporate battery 234 to a printed circuit board assembly (PCBA), e.g., on which one or more components of sensor electronics module 106 reside. Yet, in some other implementations, the one or more components of the sensor electronics module 106 maybe imprinted or formed on a flex electronics platform (e.g., stretchable electronic technology that may enable components of the sensor electronics module to be formed on bendable substrates, such as sheets of plastic or steel foil). In some examples, silicon nanoribbon elastomeric polymer material may be used to generate the flex or stretchable electronics of the sensor electronics module 106. The use of flex circuit technology negates the conventional need to have battery 234 hard-soldered onto the PCBA allowing battery 234 to be positioned thereon more freely, which in turn allows for more flexibility with regard to the shape of sensor electronics module 106, as well as a reduction in the size of the sensor electronics module 106. Moreover, during conventional installation of a battery on a PCBA, the battery is typically hard-soldered and epoxied onto the PCBA. Because the battery may have different heat characteristics from surrounding circuitry, the heating of the battery due to the epoxy process can cause flexing of the PCBA and/or other components installed thereon. In contrast, use of flex circuit technology allows battery 234 to move or be flexible during the epoxy hardening process without affecting the surrounding circuitry. It is contemplated that, battery 234 may be stretchable and may be charged wirelessly. Moreover, for example, the implementation of flex circuit technology (e.g., optionally with the PCBA) for sensor electronics module 106 may allow the analyte sensor system 104 to utilize near field communication (NFC) technology to configure electronic components of the sensor electronics module 106, e.g., including activating certain chips and/or data communications with certain chips. Yet in another implementation, it is contemplated that ambient backscatter technology may be implemented with the flex sensor electronics module 106 to facilitate data communication without the use of batteries. It is noted that, sensor electronics module 106 using flex electronics technology may withstand compression better and may accommodate twisting or bending motion, thereby providing improved connection to the sensor wire and signal acquisition and transmission.

A battery charger and/or regulator 236 may be configured to receive energy from an internal and/or external charger. In some embodiments, a battery regulator (or balancer) 236 regulates the recharging process by bleeding off excess charge current to allow all cells or batteries 234 in the sensor electronics module 106 to be fully charged without overcharging other cells or batteries. In some embodiments, the battery (or batteries) 234 is configured to be charged via an inductive and/or wireless charging pad. One skilled in the art appreciates a variety of known methods of charging batteries, which can be implemented with the system described herein, including wired (cable/plug) and wireless methods.

One or more communication ports 238, also referred to as external connector(s), can be provided to allow communication with other devices, for example a PC communication (com) port can be provided to enable communication with systems that are separate from, or integral with, the sensor electronics module 106. The communication port, for example, may comprise a serial (e.g., universal serial bus or "USB") communication port, allows for communicating with another computer system (e.g., PC, smart mobile phone, personal digital assistant or "PDA," server, or the like). In one exemplary embodiment, the sensor electronics module 106 is able to transmit historical data to a separate computing device for retrospective analysis by a patient and/or physician.

In conventional continuous analyte sensor systems, the on-skin portion of the sensor electronics is generally simplified to minimize complexity and/or size of on-skin electronics, for example, providing only raw, calibrated, and/or filtered data to a display device 120a-e configured to run calibration and other algorithms required for displaying sensor information. In contrast, the sensor electronics module 106 executes prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor information, set modes of operation, evaluate the data for aberrancies, and/or the like, which are described in more detail in U.S. Pat. No. 7,310,544, 6,931,327, U.S. Patent Publication No. US-2005-0043598-A1, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Patent Publication No. US-2005-0154271-A1, U.S. Patent Publication No. US-2005-0192557-A1, U.S. Patent Publication No. US-2006-0222566-A1, U.S. Patent Publication No. US-2007-0203966-A1 and U.S. Patent Publication No. US-2007-0208245-A1, each of which is incorporated herein by reference in its entirety. Furthermore, the sensor electronics module 106 is configured to store the transformed sensor data (e.g., estimated analyte values, trend information) and to communicate the sensor information to a plurality of different display devices 120a-e. In some embodiments, the display devices are "dummy" devices, namely, they are configured to display the sensor information as received from sensor electronics module 106, without any additional sensor data processing.

Figure 2B:
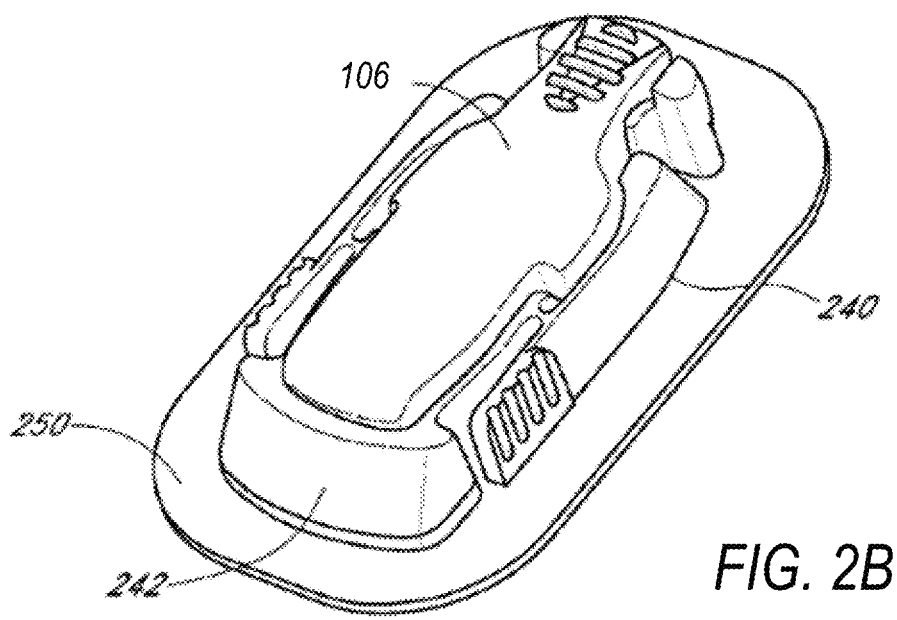
FIGS. 2B and 2C are a perspective view and side view of the example sensor electronics module of FIG. 2A.
Figure 2C:
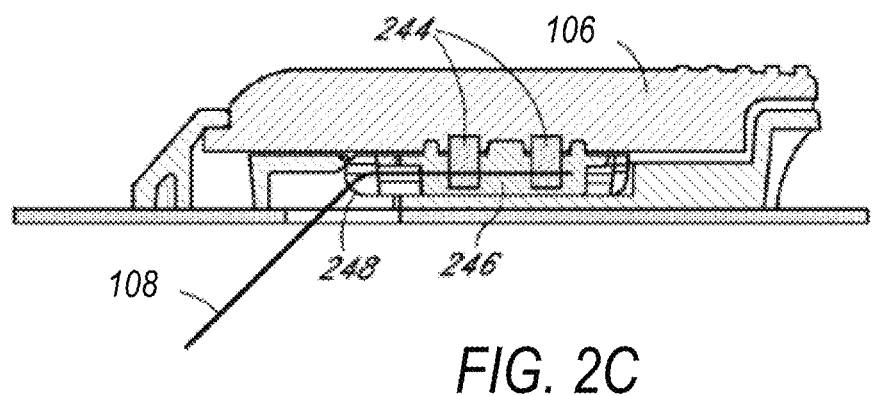

FIGS. 2B and 2C are perspective and side views of analyte sensor system 104 including a mounting unit 240 and sensor electronics module 12 attached thereto in some embodiments, shown in its functional position, including a mounting unit and a sensor electronics module matingly engaged therein. In some embodiments, the mounting unit 240, also referred to as a housing or sensor pod, comprises a base 242 adapted for fastening to a host's skin. The base 242 can be formed from a variety of hard or soft materials, and preferably comprises a low profile for minimizing protrusion of analyte sensor system 104 from host 102 during use. In some embodiments, the base 242 is formed at least partially from a flexible material, which is believed to provide numerous advantages over conventional transcutaneous sensors, which, unfortunately, can suffer from motion-related artifacts associated with movement of host 102, when host 102 is using analyte sensor system 104. The mounting unit 240 and/or sensor electronics module 106 can be located over the sensor insertion site to protect the site and/or provide a minimal footprint (utilization of surface area of the host's skin).

In some embodiments, a detachable connection between the mounting unit 240 and sensor electronics module 106 is provided, which enables improved manufacturability, namely, the relatively inexpensive mounting unit 240 can be disposed of when replacing continuous analyte sensor 108 after its usable life, while the relatively more expensive sensor electronics module 106 can be reusable. In some preferred embodiments, the sensor electronics module 106 is configured with signal processing (programming), for example, configured to filter, calibrate and/or other algorithms useful for calibration and/or display of sensor information, as alluded to previously. However, an integral (non-detachable) sensor electronics module 106 can be configured in accordance with other embodiments.

In some embodiments, the contacts 244 are mounted on or in a subassembly hereinafter referred to as a contact subassembly 246 configured to fit within the base 242 of the mounting unit 240 and a hinge 248 that allows the contact subassembly 246 to pivot between a first position (for insertion) and a second position (for use) relative to the mounting unit 240. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 244 are formed from a conductive elastomeric material, such as a carbon black elastomer, through which continuous analyte sensor 108 extends.

In certain embodiments, the mounting unit 240 is provided with an adhesive pad 250, disposed on the back surface of mounting unit 240 and including a releasable backing layer. Thus, removing the backing layer and pressing the base portion 242 of the mounting unit 240 onto the skin of host 102 adheres the mounting unit 240 to the skin of host 102. Additionally or alternatively, an adhesive pad 240 can be placed over some or all of the analyte sensor system 104 after insertion of continuous analyte sensor 108 is complete to ensure adhesion, and optionally to ensure an airtight seal or watertight seal around the wound exit-site (or insertion site) (not shown). Appropriate adhesive pads can be chosen and designed to stretch, elongate, conform to, and/or aerate the region (e.g., the skin of host 102). The embodiments described with reference to FIGS. 2B and 2C are described in more detail with reference to U.S. Pat. No. 7,310,544, which is incorporated herein by reference in its entirety.

Wireless Communications

Figure 3:
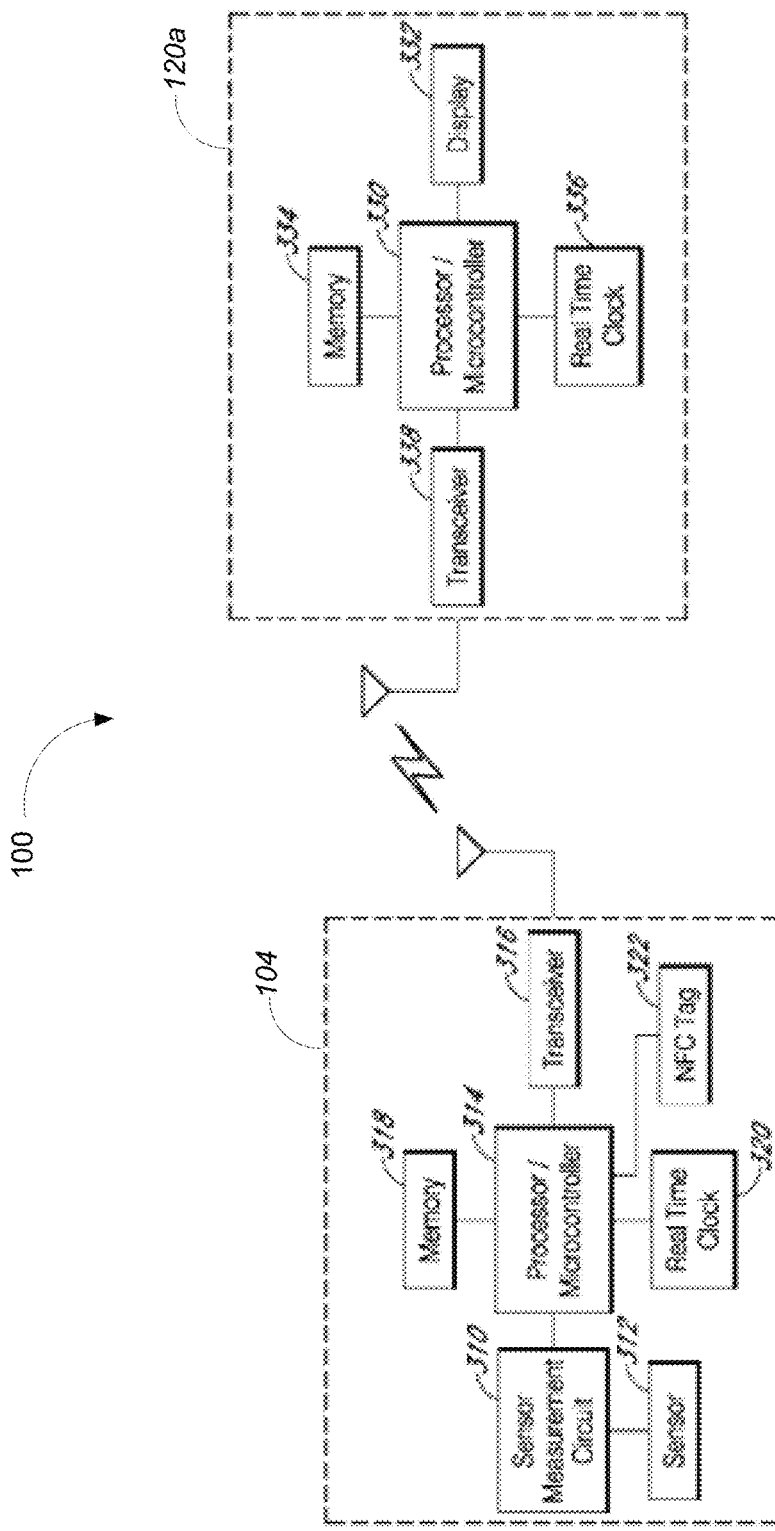
FIG. 3 is a block diagram illustrating elements of an example continuous analyte monitoring system and a display device in communication with each other in accordance with various embodiments of the present disclosure.

FIG. 3 is a block diagram illustrating example components of analyte sensor system 104 and at least one of the plurality of display elements 120a, as well as the communications therebetween. The analyte sensor system 104 may include an implantable continuous analyte sensor 312 (one embodiment of continuous analyte sensor 108 of FIG. 1) coupled to a sensor measurement circuit 310 for processing and managing sensor data. The sensor measurement circuit 310 may be coupled to a processor 314 (part of sensor electronics module 106 in FIG. 1). In some embodiments, the processor 314 may perform part or all of the functions of the sensor measurement circuit 310 for obtaining and processing sensor measurement values from the implantable continuous sensor 312. The processor may be further coupled to a radio unit or transceiver 316 (part of sensor electronics module 106 in FIG. 1) for sending sensor information to and receiving requests and commands from an external device, such as display device 120a, which is used to display or otherwise provide the sensor information to a user. As used herein, the terms "radio unit" and "transceiver" are used interchangeably and generally refer to a device that can wirelessly transmit and receive data. The analyte sensor system 104 may further include a memory 318 (also part of sensor electronics module 106 in FIG. 1) and a real time clock (RTC) 320 (again, part of sensor electronics module 106 in FIG. 1) for storing and tracking sensor information. In some embodiments, analyte sensor system 104 further includes near field communication (NFC) capability. In some embodiments, an NFC tag 322 is implemented/integrated into the electronics in analyte sensor system 104 or embedded in e.g., the housing or mounting unit 240. While not shown explicitly, NFC tag 322 may be included as part of transceiver 316, making transceiver 316 a "smart transceiver."

Wireless communication protocols may be used to transmit and receive data between analyte sensor system 104 and display device 120a. The wireless communication protocol used may be designed for use in a wireless sensor network that is optimized for periodic and small data transmissions (that may be transmitted at low rates if necessary) to and from multiple devices in a close range (e.g., a personal area network (PAN)). For example, the wireless communication protocol may be optimized for periodic data transfers where transceivers may be configured to transmit data for short intervals and then enter low power modes for long intervals. The wireless communication protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The wireless communication protocol may further be configured to establish communication channels with multiple display devices, e.g., two or more of display devices 120a-e, while implementing interference avoidance schemes. In some embodiments, the wireless communication protocol may make use of adaptive isochronous network topologies that define various time slots and frequency bands for communication with several ones of display devices 120a-e. The wireless communication protocol may thus modify transmission windows and frequencies in response to interference and to support communication with multiple ones of display devices 120a-e. Accordingly, the wireless protocol may use time and frequency division multiplexing (TDMA) based schemes. The wireless communication protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless communication protocol may operate in various frequency bands such as an open ISM band such as 2.4 GHz. Furthermore, to reduce power usage, the wireless communication protocol may adaptively configure data rates according to power consumption.

Display device 120a may be used for alerting and providing sensor information to a user, such as host 102, and may include a processor 330 for processing and managing sensor information. Display device 120a may include a display 332, a memory 334, and a real time clock 336 for displaying, storing and tracking sensor information, respectively. Display device 120a may further include a radio unit or transceiver 338 for receiving sensor information and for sending requests, instructions, and data to the analyte sensor system 104. The transceiver 338 may further employ a wireless communication protocol. The memory 334 may also be used for storing an operating system and/or a custom (e.g., proprietary) application designed for wireless data communication between a transceiver, e.g., transceiver 316 and display device 120a. The memory 334 may be a single memory device or multiple memory devices and may be a volatile or non-volatile memory for storing data and/or instructions for software programs and applications. The instructions may be executed by the processor 330 to control and manage the transceiver 338.

It should be understood that in the case of display device 120e, which may be a medicament delivery device in addition to or instead of a display device, the alerts and/or sensor information provided by continuous analyte sensor 108 vis-à-vis sensor electronics module 106, can be used to initiate and/or regulate the delivery of the medicament to host 102.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processors 314 and 330 do not need to manage these activities, but rather provide desired data values for transmission, and manage high level functions such as power up or down, set a rate at which messages are transmitted, and the like. Instructions and data values for performing these high level functions can be provided to the transceiver circuits 316 and 338, respectively, via a data bus and transfer protocol established by the manufacturer of the transceiver circuits 316 and 338.

Components of the analyte sensor system 104 may require replacement periodically. For example, implantable continuous analyte sensor 312 that may be attached to sensor electronics module 106 which itself includes the sensor measurement circuit 310, the processor 314, memory 318, and transceiver 316, and battery (not shown) may require periodic replacement (e.g., every 7-30 days). The sensor electronics module 106 may be configured to be powered and active for much longer than implantable continuous analyte sensor 312 (e.g., for 3 months, 6 months or more) until the battery needs replacement. Replacing these components may be difficult and require the assistance of trained personnel. Reducing the need to replace such components, including the battery if replaceable, significantly improves the convenience of the analyte sensor system 104 to the host 102.

When sensor electronic module 106 is used for the first time (or reactivated once a battery has been replaced in some cases), it may be connected to implantable continuous analyte sensor 312. As will be further described below, there may be a process for initially establishing communication between display device 120a and sensor electronics module 106 when it is first used or re-activated (e.g., the battery is replaced). Once display device 120a and sensor electronics module 106 have established communication, display device 120a and sensor electronics module 106 may periodically and/or continuously be in communication over the life of several ones of implantable continuous analyte sensor 312 until, for example, the battery or the entirety of sensor electronics module 106 needs to be replaced. Each time continuous analyte sensor 312 is replaced, notifications of a new continuous analyte sensor 312 can be sent/exchanged via the previously established communication between the sensor electronics module 106 and display device 120a.

In accordance with one embodiment, analyte sensor system 104 gathers and processes analyte measurements from continuous analyte sensor 312, and periodically sends sensor information representative of the analyte measurements to display device 120a. Measurements are gathered and transmitted over the life of continuous analyte sensor 312 (e.g., in the range of 1 to 30 days or more). New measurements may need to be transmitted often enough to adequately monitor analyte levels. Rather than having the transmission and receiving circuitry of each of the analyte sensor system 104 and display device 120a continuously communicating, the analyte sensor system 104 and display device 120a may regularly and periodically establish a communication channel between them. Thus, analyte sensor system 104 can communicate wirelessly with display device 120a at predetermined time intervals. The duration of the predetermined time interval can be selected to be long enough so that the analyte sensor system 104 does not consume too much power by transmitting data more frequently than needed, yet frequent enough to provide substantially real-time sensor information (e.g., measured analyte values) to one or more of display devices 120a-e for output (e.g., display) to a user. While the predetermined time interval is every five minutes in some embodiments, it is appreciated that this time interval can be varied to be any desired length of time. It should be noted that other contemplated embodiments involve irregular or aperiodic transmissions of sensor information, e.g., from analyte sensor system 104 to one or more of display devices 120a-e.

Figure 4:
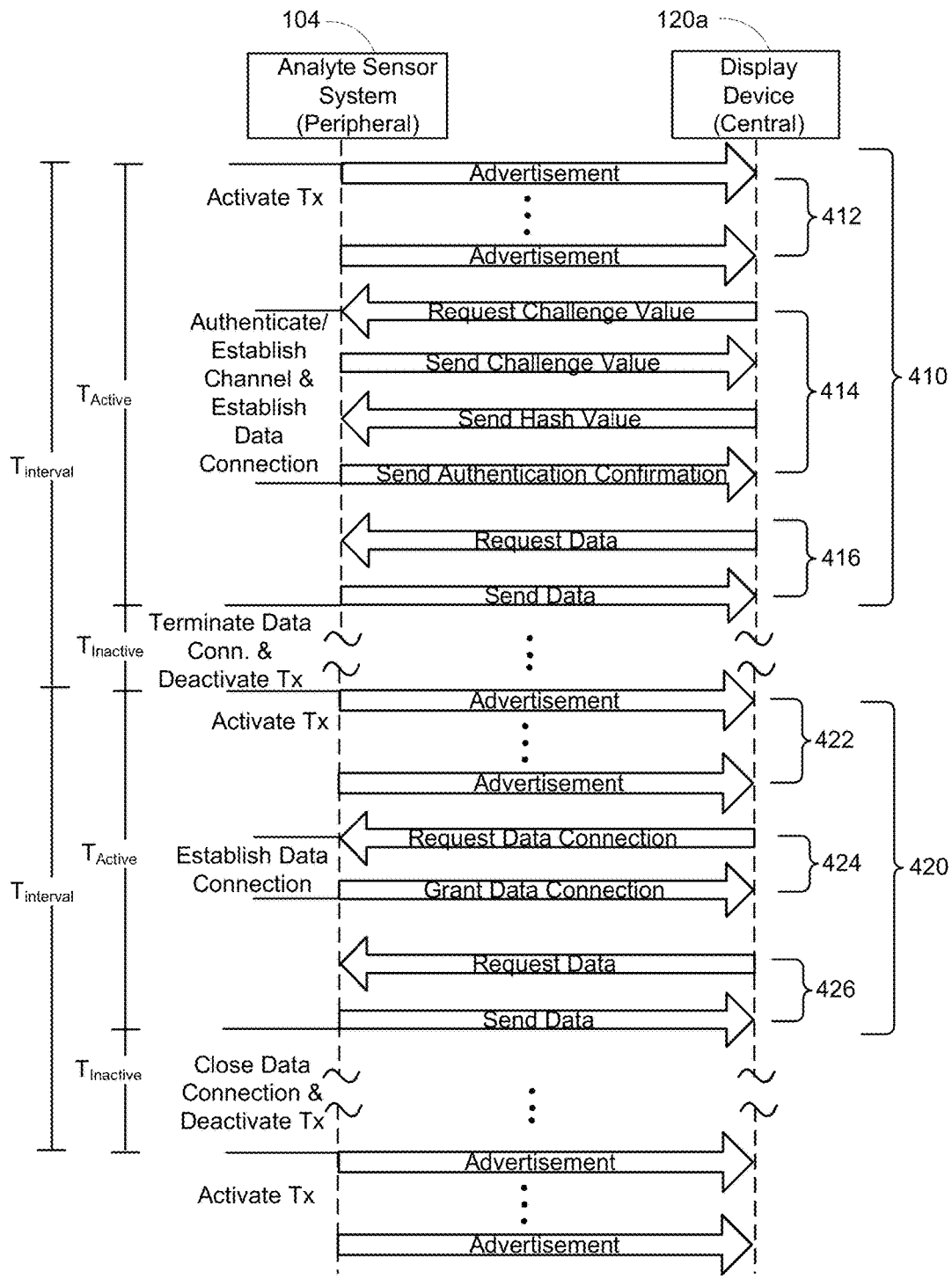
FIG. 4 is an example advertising/connection sequence in accordance various embodiments described in the present disclosure.

FIG. 4 is an example advertising/connection sequence between analyte sensor system 104 and one or more of the display devices (e.g., display device 120a) which is capable of wirelessly receiving analyte measurement values from the analyte sensor system 104 according to certain aspects of the present disclosure. The various tasks performed in connection with the advertising/connection illustrated in FIG. 4 may be performed by a processor executing instructions embodied in a non-transitory computer-readable medium. For example, the tasks performed in connection with the procedure may be performed by hardware, software, firmware, or any combination thereof incorporated into one or more of computing devices, such as analyte sensor system 104 and display device 120a of FIG. 1 and/or FIG. 3. It should be appreciated that the procedure may include any number of additional or alternative tasks. The tasks shown in FIG. 4 need not be performed in the illustrated order, and the procedure may be incorporated into a more comprehensive procedure or process having additional functionality not described in detail herein.

In the example described below, the analyte values are glucose values based on one or more measurements of glucose levels by the implantable continuous analyte sensor 312 for illustration purposes. However, it should be understood that the analyte values can be any other analyte value described herein. The wireless data communication between the analyte sensor system 104 and the display device 120a may happen periodically, at times separated by an update interval denoted "$T_{interval}$" that may correspond to a time duration between two consecutive wireless communication sessions between the transceiver 316 of the analyte sensor system 104 and the transceiver 338 of display device 120a. Alternatively, the update interval may be thought of as a period of obtaining and sending a recently measured glucose value. Transmitting advertisement signals, establishing a data connection (e.g., a communication channel) and requesting and sending data may occur during wireless communication sessions each lasting an active time or period denoted "$T_{Active}$" within an update interval $T_{interval}$. In between two consecutive wireless communication sessions, the transceiver 316 goes into an inactive or sleep mode for an inactive period denoted as "$T_{Inactive}$" to conserve battery life and/or reduce peak voltage requirements, for example.

FIG. 4 shows two such wireless communication sessions, namely, a first wireless communication session 410 and a second wireless communication session 420. Each wireless communication session 410, 420 starts with the analyte sensor system 104 establishing a data connection with display device 120a. To establish a data connection with display device 120a, the transceiver 316 of the analyte sensor system 104 transmits a series of advertisement signals 412 during the first wireless communication session 420. Each advertisement signal may be considered an invitation for display device 120a to establish a data connection with the transceiver 316. In some embodiments, advertisement signals 412 may be embodied as advertising beacons, as will be discussed in greater detail below.

In the illustrated example of FIG. 4, it is assumed that the analyte sensor system 104 needs to engage in an initial system setup because the analyte sensor system 104 has been just turned on for the first time and/or is not current paired with display device 120a. Typically, a user of display device 120a identifies a new or never-been used analyte sensor system 104 that needs to be paired with display device 120a by entering identification information (e.g., a serial number) associated with the new/unpaired analyte sensor system 104 via a custom application running on display device 120a using a user interface (e.g., a touchscreen display). During the first wireless communication session 410, an authentication procedure needs to be performed as part of a data connection process 414. To establish a data connection with the analyte sensor system 120, the display device 120a listens continuously until an advertisement signal transmitted by the transceiver 316 of the analyte sensor system 104 is received. Once the transceiver 316 begins transmitting advertisement signals 412, it may take one, two, or more advertisement signals for the display device 120a to receive at least one of the advertisement signals and respond to at least one of the advertisement signals. In some embodiments, the transceiver 316 stops sending additional advertisement signals once display device 120a receives an advertisement signal and responds to that advertisement signal, for example, via an acknowledgement. In other embodiments, the transceiver 316 may continue to send additional advertisement signals even after receiving a response from display device 120a so that another display device, e.g., one or more of display devices 120b-e, may receive and respond to at least one of the additional advertisement signals.

After an advertisement signal is successfully received by display device 120a, display device 120a and the analyte sensor system 104 engage in a first data connection process 414. During the first data connection process 414, the display device 120a requests a challenge value from the analyte sensor system 104 and the analyte sensor system 104 sends the change value to the display device 120a in response. Upon receiving the challenge value, the display device 120a calculates a hash value based on the challenge value and the identification information associated with the analyte sensor system 104 and/or the transceiver 316 and sends the hash value to the transceiver 316. The transceiver 316 receives the hash value from the display device 120a, decodes the identification information from the hash value, and verifies that the received identification information matches identification information associated with the analyte sensor system 104 and/or transceiver 316 previously stored in the memory 318 of the analyte sensor system 104, such as during manufacturing of the analyte sensor system 104. Upon verification, the transceiver 316 sends a signal confirming a successful authentication to the display device 120a. Once authenticated, the analyte sensor system 104 and display device 120a may exchange information to determine how data will be exchanged (e.g., a specific frequency, time slot assignment, encryption, etc.).

After completion of the first data connection process 414, the analyte sensor system 104 and now-connected display device 120a engage in a first data communication 416 during which display device 120a requests and receives desired information (e.g., analyte measurement data, control information, identification information, and/or instructions) from the analyte sensor system 104. When the first data communication 416 is completed, the data connection is terminated (e.g., by closing the established communication channel) and the transceiver 316 and/or the processor 314 of the analyte sensor system 104 (and possibly the transceiver 338 and/or the processor 330 of the display device 120a as well, depending on implementation preference) can be deactivated by causing the transceiver 316 and/or the processor 314 to enter a sleep or inactive mode. In some embodiments, the transceiver 316 is completely powered down during a sleep mode. In other embodiments, the transceiver 316 is in a low power mode using only a small fraction (e.g., 1-10%) of the normal current/power. As will be discussed further below, transceiver 316 may be woken up, for example, by an NFC on-demand request for sensor information to be sent to display device 120a, accelerometer movement that triggers a wake up of transceiver 316, etc.

The active period $T_{Active}$ corresponding to a duration of each wireless communication session may be a small fraction of the update interval $T_{interval}$ corresponding to a period between two consecutive wireless communication sessions. For example, $T_{interval}$ may be between about 200 and 400 seconds and $T_{Active}$ may be between 20 and 40 seconds. As such, the transceiver 316 of the analyte sensor system 104 may be powered fully for only 10 percent (e.g., 30 seconds) of a five minute $T_{interval}$. This may significantly reduce power consumption and peak voltage demand. In some cases, the transceiver 316 is not completely powered down, but enters a low-power mode when not transmitting. After an inactive time or period $T_{Inactive}$, a second wireless communication session 420 starts when the transceiver 316 (and the transceiver 338) powers up again, begins transmitting a second series of advertisement signals 422, engages in a second data connection process 424 and a second data communication process 426 with the transceiver 338 of display device 120a as shown in FIG. 4. Unlike the first data connection process 414, however, the second data connection process 424 does not involve an authentication procedure because the analyte sensor system 104 and the display device 120a have been successfully paired or bonded during the first wireless communication session 410 as described above. This process may continue, with new data connections and communications being completed at the predetermined intervals. During all or part of each inactive period $T_{Inactive}$ during which the transceiver 316 is in a sleep mode, the processor 314 can take measurement(s) of one or more analyte values using the analyte sensor 312 and the sensor measurement circuitry 310. For example, the processor 314 may take multiple analyte value measurements and average them to generate a single averaged analyte value to be transmitted in a next wireless communication session.

Continuously re-establishing a new communication channel to allow for partially or wholly powering down the transceiver 316 during each update interval $T_{interval}$ can provide significant power savings and can allow the sensor electronics module 106 (FIG. 1) to operate continuously for, e.g., 1 month, 3 months, 6 months, 1 year, etc., without requiring a battery replacement. It should be noted that in some embodiments, battery replacement may be a function of the actual expiration of battery power or some predetermined level of remaining battery power. Furthermore, rather than blindly transmitting glucose data points during the update interval $T_{interval}$, establishing specific data connections (e.g., communication channels) with only desired display devices, e.g., display device 102a, can prevent unauthorized use and interception of glucose measurement values. In some embodiments, only a subset of multiple display devices 120a-e can be configured to receive different data such as glucose measurement values and/or alarm conditions. This has a benefit of preventing all of display devices 120a-e from issuing alarms, thereby confusing and/or frustrating the user. In addition, by establishing a secure two-way communication channel, requests for specific glucose measurement values or communication of calibration or configuration information may be transmitted on an as-needed/requested basis between the analyte sensor system 104 and display device 120a.

Also, in some embodiments, the transceiver 316 may not be activated for data communication every update interval $T_{interval}$. Instead, the transceiver 316 may be activated every second, third or fourth update interval $T_{interval}$, for example, so that communication between the analyte sensor system 104 with the display device 120a occurs less frequently than every update interval $T_{interval}$. Doing so can further reduce power consumption. Activation could also depend on the sensor information. For example, the transceiver 316 need only be activated if data meets certain thresholds, such as a current rate of change, current high value, current low value, absolute difference from a previously exchanged value, percentage difference from a previously exchanged value, and the like. In some embodiments, instead of skipping certain fixed update intervals, the length of each interval can be made to vary based on the sensor information or other criteria. For example, if the sensor information indicates a low glucose value and/or a hypoglycemic reaction is detected, the update interval value can be shortened from a normal (longer) update interval value so that more frequent readings are taken and/or transmitted.

In some embodiments, the update interval $T_{interval}$, the active period $T_{Active}$ and a frequency $F_{Activation}$ by which the transceiver is activated (e.g., every second, third or fourth update interval) may be variable. In certain embodiments, the above-identified parameters can be user configurable (e.g., by inputting a value for the variable using user interface of display device 120a) and/or automatically varied by the analyte sensor system 104 or display device 120a based on one or more criteria. The criteria can include: (i) a monitored battery power of the sensor system 104, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 104 or display device 120a and (x) type of display device 120a.

$T_{interval}$, $T_{Active}$, $F_{Activation}$ and/or other configuration items described herein may form part of a communication protocol profile that may be stored on any device that implements the fundamental communication protocol to allow for a customized use of the protocol for communicating analyte measurement values in the analyte sensor system 104 and one or more of display devices 120a-e.

Power Savings

As discussed above, reducing the need to replace components significantly improves the convenience of the analyte sensor system 104 to the user. Accordingly, various embodiments are directed to power saving schemes and/or mechanisms to increase battery life of one or more aspects analyte sensor system 104, e.g., sensor electronics module 106.

Battery Activation

Consuming power while electronic components, such as those in sensor electronics module 106 (FIG. 2A), are not in normal use (e.g., while in storage prior to use) can drain valuable battery power; particularly if, for example, battery 234 is a non-rechargeable and/or non-replaceable type of battery. Indeed, the amount of power available to sensor electronics module 106 can be a limiting factor as to the life of sensor electronics module 106 and/or what features can be incorporated into sensor electronics module 106. Thus, the amount of power consumed by sensor electronics module 106 while in storage may not only limit its useful life, but can also limit its capabilities.

Accordingly, some embodiments are directed to delaying activation of battery 234. In this way, battery 234 can be left in an undischarged state for as long as possible to mitigate the loss of battery life. To achieve such delayed activation of battery 234, some embodiments utilize a battery activation circuit that keeps battery 234 from discharging subsequent to installation in sensor electronics module 106 until such time that a manufacturer is ready to complete the assembly process of sensor electronics module 106 (e.g., to create a final "encapsulated" unit).

Figure 5A:
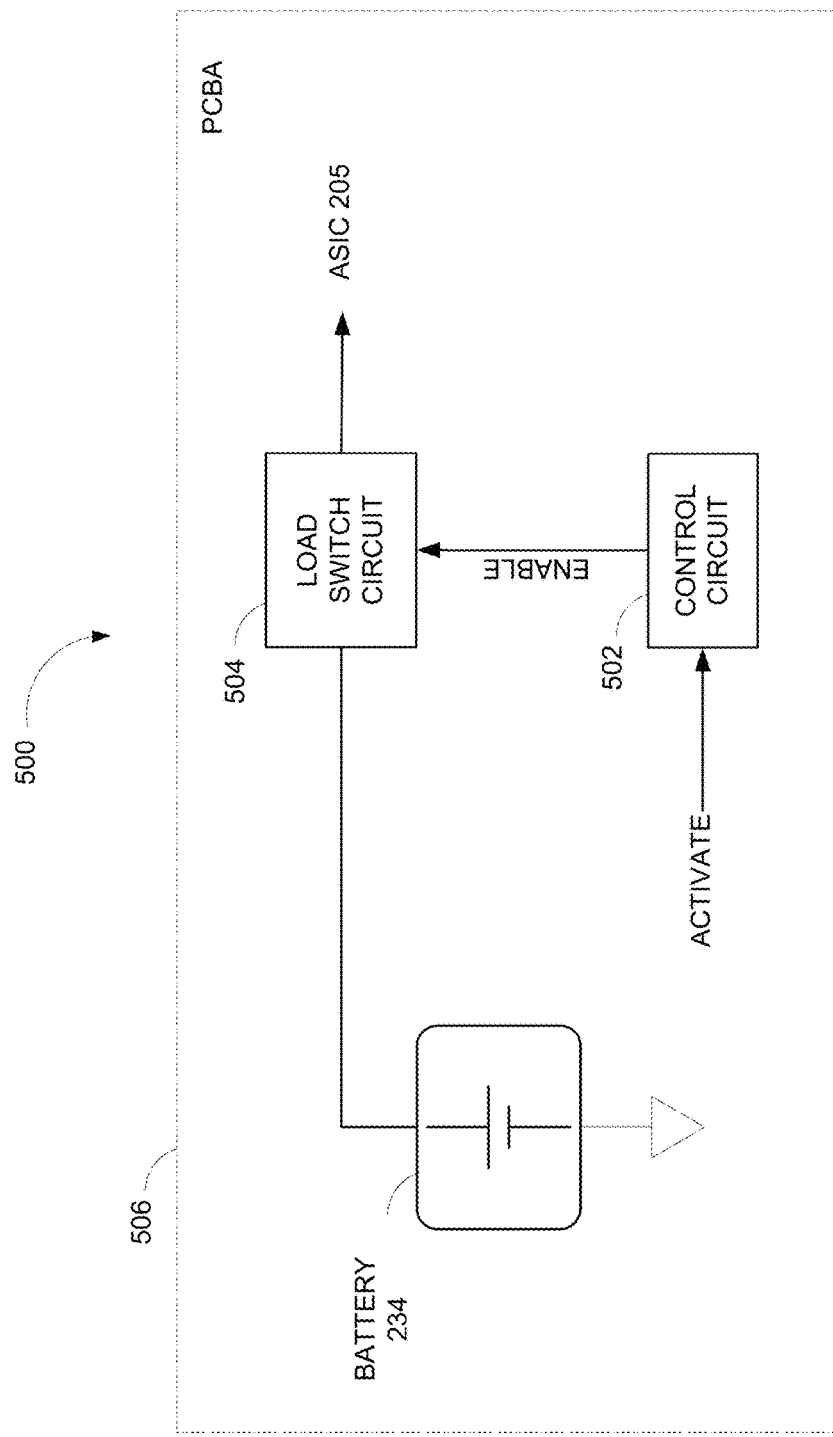
FIG. 5A is a block diagram illustrating a battery activation circuit for the example sensor electronics module of FIG. 2A.

FIG. 5A illustrates an example battery activation circuit 500 in accordance with one embodiment. In the example embodiment, battery activation circuit 500 includes a control circuit 502 in communication with load switch circuit 504 to enable/disable the circuit 504, which electrically couples battery 234 to the circuitry of sensor electronics module 205, e.g., shown as ASIC 205 in this example. In some implementations, control circuit 502 may be configured to operate in a default state such that control circuit 502 produces a signal that disables load switch circuit 504. With load switch circuit 504 disabled, battery 234 is effectively disconnected from the circuitry of sensor electronics module 106, e.g., ASIC 205 (shown in FIG. 2A). In this default state, no current flows from battery 234. Accordingly, a Printed Circuit Board Assembly (PCBA) 506 including battery activation circuit 500 and sensor electronics module 106 could be stored for several months while retaining nearly all of the battery capacity, for example, of battery 234. When functional testing of PCBA 506 is complete and the manufacturer is ready to complete the assembly process as described above, a one-time activate signal is provided to control circuit 502. This may entail a point during the manufacturing process when assembly of sensor electronics module 106 is near completion (such as prior to encapsulating the one or more components of sensor electronics module 106 such that battery 234 and/or the leads connected to battery 234 will become inaccessible). The one-time activate signal can be provided by a tester/testing mechanism. In response to such an activate signal, control circuit 502 is configured to produce another signal that enables load switch circuit 504, thereby allowing current to flow from battery 234 to the circuitry, e.g., ASIC 205, of sensor electronics module 106.

In addition to delaying activation of battery 234, use of battery activation circuit 500 allows for the aforementioned automated activation, which in turn negates the need for human or robotic operators to perform manual soldering or jumper installation to complete connection of battery 234 to PCBA 506. Thus, savings in manufacturing costs can be realized while also reducing manufacturing time.

In embodiments where battery 234 is a rechargeable/replaceable type battery, conventional systems are unable to determine whether battery 234 is optimal. That is, existing systems cannot determine whether battery 234 is of a type that provides sufficient/desirable level of power for a sufficient/desirable amount of time when powering analyte sensor system 104. For example, battery original equipment manufacturers (OEMs) may utilize higher quality components, employ stricter quality control, etc., to produce batteries that can meet the requirements of devices, such as analyte sensor system 104. On the other hand, non-OEM battery producers or the like may produce batteries that could result in, at best, sub-optimal operation of analyte sensor system 104, and at worst, damage analyte sensor system 104 and/or harm the user, as a result of the damage or by virtue of providing inaccurate sensor information.

Thus, some embodiments may determine whether or not battery 234 is an authentic or allowed battery. In particular, a battery authentication circuit can be implemented in sensor electronics module 106 for authenticating a replacement battery 234. It is presumed that a manufacturer of analyte sensor system 104 will be utilizing an appropriate battery 234, but battery authentication can be utilized for any battery 234, whether battery 234 is originally installed during the manufacturing of analyte sensor system 104 or for a replacement battery 234'.

Figure 5B:
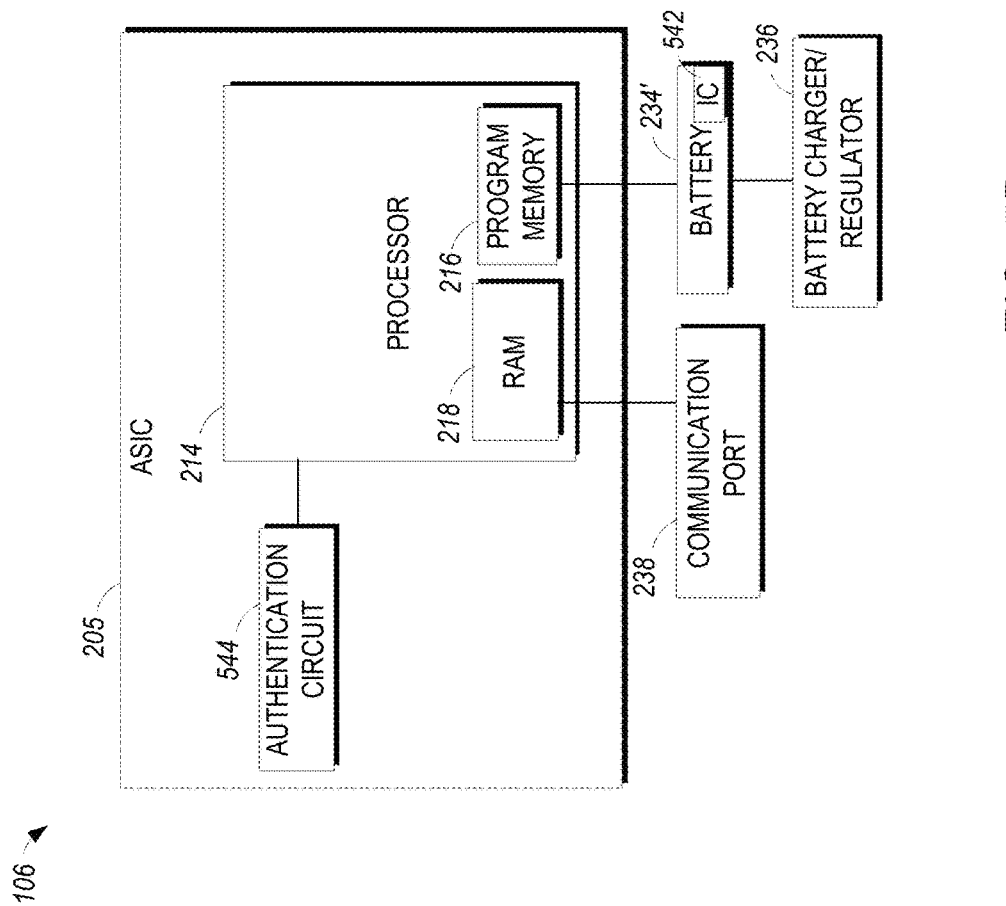
FIG. 5B is a block diagram illustrating a battery authentication feature of the example sensor electronics module of FIG. 2A

FIG. 5B illustrates sensor electronics module 106 (also illustrated in FIG. 2A), where some components have been removed for ease of illustration and understanding. Replacement battery 234' may have incorporated therein, a battery integrated circuit (IC) 542. This battery IC 542 may be integrated into a housing or wrap that encapsulates replacement battery 234'. Upon installation of replacement battery 234', authentication circuit 544 can instruct processor 214 to read authentication data of replacement battery 234' from battery IC 542. Such authentication data may include, for example, an identification code, cyclic redundancy check value, etc., although any type of identifying information may be used to authenticate replacement battery 234'. Identifying information received from replacement battery 234' can be checked against identifying information maintained in a memory of processor 214, e.g., program memory 216, or obtained via a remote data store via communication port 238. In some examples, the memory (e.g., program memory 216 or RAM 218) may store verification information, such as, battery life information that indicates the required amount of power that will be appropriate for operating the sensor electronics module 106. In one example, upon installation of a new battery (e.g., a replacement battery 234'), authentication circuit may instruct processor 214 to process such battery life information (e.g., from the battery IC 542) for the replacement battery 234' and compare with the stored battery life information. Comparisons may be made to verify and/or to determine whether the replacement battery 234' is suitable for operating the sensor electronics module 106. It is noted that, in some implementations, a combination of identification information and verification information may be utilized by the authentication circuit 544 and/or processor 214 to determine the authentication of the battery (e.g., replacement battery 234').

It should be noted that in order to perform battery authentication, analyte sensor system 104 should be operational, i.e., receiving power from replacement battery 234'. Thus, replacement battery 234' may be used to temporarily power analyte sensor system 104 for the purposes of authenticating replacement battery 234'. Should authentication fail, operation of analyte sensor system 104 can be inhibited. It should further be noted that authentication circuit 544 circuit can be implemented in battery charger/regulator 236. That is, a user, e.g., host 102, may be required to attach battery charger/regulator 236 to sensor electronics module 106 upon installation of a replacement battery, e.g., replacement battery 234' to ensure that replacement battery 234' is properly charged/operational. Implementing authentication circuit 544 in battery charger/regulator 236 can negate the need to increase the physical size of sensor electronics module 106 and maintain as small a footprint as possible.

Further still, off-the-shelf/OEM batteries, although providing consistent performance as described above, may still not be optimized for at least some of the types of operations performed by analyte sensor system 104, e.g., multiple wireless connections to display devices 120a-e. Thus, in some embodiments, different configuration/operational modes may be selected depending on the type of replacement battery 234' installed in analyte sensor system 104.

Yet another issue that can arise in the context of using battery 234 to power analyte sensor system 104 is the issue of high current drain. There can be times when analyte sensor system 104 falls into a mode of operation where a large amount of current is drawn (e.g., during active periods, as well as during periods when analyte sensor system 104 is in a sleep or low power mode). This current drain results in battery 234 being drained sooner than expected.

Accordingly, some embodiments can detect such high current modes. In particular, some embodiments monitor the general purpose input/output (GPIO) ports/pins to detect a high current mode.

Low Power Mode Wakeup

As described above, sensor electronics module 106 can be configured such that it remains in a low power or storage mode until just before completion of the manufacturing process, e.g., prior to shipment by the manufacturer or distributor, for example, so that the sensor electronics module 106 does not consume power while sitting in storage at the manufacturer or distributor. Referring back to FIG. 4, sensor electronics module 106 may also enter low power or no power modes during certain periods of inactivity, e.g., $T_{Inactive}$ periods, e.g., in between wireless communication sessions. It should be noted that in some embodiments, one or more components making up sensor electronics module 106, such as transceiver 316 may wake up or power down, while one or more other components may remain in low power/sleep mode. In other embodiments, it may be that all the components making up sensor electronics module 106 wake up or enter a low power/sleep mode.

Waking up and powering on sensor electronics module 106 (e.g., causing sensor electronics module 106 to enter an active or operational mode, such as during $T_{Inactive}$ periods 410 and 420 of FIG. 4) can occur when a sensor reading above a predetermined threshold is detected. The predetermined threshold can be specified in terms of counts. In general, and referring back to FIG. 2A, potentiostat 210 may include a resistor (not shown) that translates current into voltage. In some embodiments, a current to frequency converter is provided that is configured to continuously integrate the measured current, for example, using a charge counting device. In some embodiments, an A/D converter digitizes the analog signal into "counts" (previously described) for processing. Accordingly, the resulting raw data stream in counts can be directly related to the current measured by the potentiostat 210.

Thus, counts may be monitored to determine whether to wake up sensor electronics module 106 to begin receiving/ obtaining and/or processing sensor information from continuous analyte sensor 108. For example, in some implementations, processor 214 of sensor electronics module 106 (or other controller chip or device of the sensor electronics module 106) may wake up periodically, e.g., every five minutes, to monitor counts. If the number of counts received is below a predetermined count threshold, processor 214 or controller may return to a low power mode. If the number of counts received exceeds the predetermined count threshold, processor 214 or controller wakes up and processes and/or forwards sensor information to telemetry module 232 to be delivered to one or more of display devices 120a-e. Also for example, in some implementations, processor 214 or other controller of the sensor electronics module 106 may remain in operational mode to monitor counts to determine whether the sensor electronics module 106 is to begin receiving/ obtaining and/or processing sensor information from continuous analyte sensor 108.

However, basing the waking up of sensor electronics module 106 on a predetermined count threshold can result in false wakeups or missed wakeups. That is, if the predetermined count threshold is too low, sensor electronics module 106 may wake up in situations when it should remain in low power or storage mode. On the other hand, if the predetermined count threshold is set too high, sensor electronics module 106 may fail to wake up when it should. Thus, some embodiments rely on a benchmarked count threshold of approximately X counts (e.g., 9000 counts) which would generally be received over the application of current for approximately Y seconds or minutes (e.g., 300 seconds or 5 minutes). In still other embodiments, the benchmarked count threshold can be monitored in the context of a persistent condition, where the benchmarked count threshold should be met or exceeded for a predetermined amount of time to ensure that sensor electronics module 106 should indeed wake up. For example, the persistent condition can include a consistent frequency of counts over a subset of the Y time duration. For example, this can ensure that the benchmarked count threshold is not reached based on an undesired anomaly, such as a spike of counts within the Y time period for monitoring the counts.

Figure 5C:
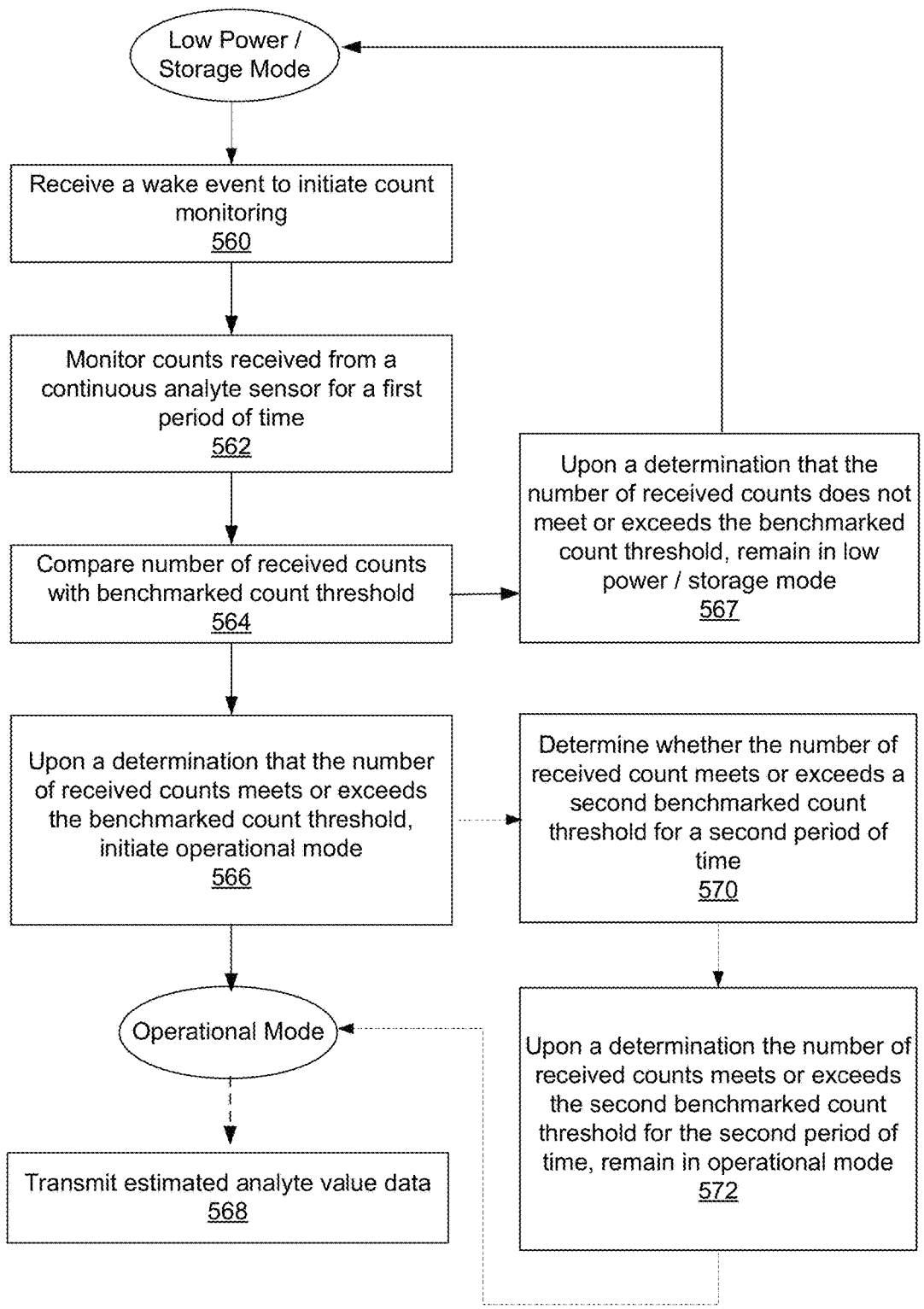
FIG. 5C is a flow chart illustrating example operations performed for waking up the example sensor electronics module of FIG. 2A based on persistent measured counts in accordance with various embodiments described in the present disclosure.

FIG. 5C is a flow chart illustrating example operations for waking up sensor electronics module 106 from a low power or storage mode. At operation 560, a wake event is received to indicate or check if the sensor electronics module 106 should be taken out of a low power or storage mode to an operational mode. The wake event may be generated by a wake source implemented between an AFE component, e.g., potentiostat 210 and processor 214, and received by processor 214. For example, operation 560 can be implemented to bring process 214 out of low power or storage mode, e.g., such as beginning a periodic sequence to monitor counts. For example, operation 560 can be implemented to begin a count monitoring period. In some implementations of the method, a controller (e.g., processor 214) is continuously conducting the count monitoring such that the operation 560 is not necessary. At operation 562, the counts received from continuous analyte sensor 108 (via potentiostat 210) are monitored for a first period of time (Y), e.g., approximately 5 minutes. The number of received counts is compared with a benchmarked count threshold (X), which can be approximately 9000 counts, at operation 564. At operation 566, and upon a determination that the number of received counts meets or exceeds the benchmarked count threshold X, processor 214 initiates operational mode of the sensor electronics module 106. For example, the sensor electronics module 106 may begin receiving/obtaining sensor information from continuous analyte sensor 108. In some embodiments, for example, at operation 568, estimated analyte value data is transmitted to one or more display devices 120a-e. That is, processor 214 stays active and forwards and/or processes the sensor information, i.e., counts, to telemetry module 232, for forwarding to one or more display devices 120a-e. However, if at operation 564 the determination was that the number of received counts did not meet or exceed the benchmarked count threshold X, the sensor electronics module 106 remains in low power/storage mode.

Optionally, in some implementations, and subsequent to the determination that the number of received counts meets or exceeds the benchmarked count threshold (operation 566), another determination can be made to determine whether the number of received counts meets or exceeds a second benchmarked count threshold (U) for a second period of time (V) at operation 570. For example, processor 214, or in general, sensor electronics module 106, will not wake up unless the second benchmarked count threshold U is met or exceeded for the second period of time V. That is, at operation 572, upon a determination that the number of received counts meets or exceeds the second benchmarked count threshold persistently for the second period of time, sensor electronics module 106 will remain in operational mode. In accordance with some embodiments, the second benchmarked count threshold U may be 300 counts while the second period of time V may be 10 seconds. Also, in accordance with some embodiments, the operation 572 can include determining that the second benchmarked count threshold U is met or exceeded for the second period of time V over multiple intervals (n). For example, the second benchmarked count threshold U may be 300 counts over the second period of time V of 10 seconds for six consecutive intervals (e.g., n=6). Similarly, for example, the second benchmarked count threshold U may be 300 counts over the second period of time V of 10 seconds for six non-consecutive intervals (e.g., n=6), e.g., such as for the first 10 second interval, with one or more 10 second intervals without monitoring the counts, and subsequently one or more 10 second intervals with monitoring counts, etc. until the six intervals are reached. Reading/sensing this reduced number of counts over a shortened period of time may be used to check persistence, i.e., a verification step to ensure sensor electronics module 106 is really meant to wake up from a low power storage mode due to insertion of a continuous analyte sensor 108 as opposed to a false wake up due to inadvertent contact by user 102 with sensor electronics module 106, for example. For example, the implementation of operation 570 can ensure that counts are generated indicative of real sensor data and not counts from electrostatic discharge (ESD) based data, which tends to come in bursts. In some implementations, the persistent condition is met when U/V is proportional to X/Y for one or more intervals. It should be noted that no additional components are needed to monitor counts as described above. That is, ASIC 205 is already configured to read counts during normal data acquisition, and processor 214 may be used to determine whether or not to wake sensor electronics module 106. It is contemplated that, in some implementations, processor 214 may be configured to determine and/or distinguish between events, such as, a wakeup event and an undesired or anomalous event (e.g., ESD event) based on the benchmarked threshold counts. For example, as described above, processor 214 may determine that an ESD event has occurred when the sensor counts are not consistent (e.g., the received counts are higher or lower than the benchmarked threshold counts (e.g., for the first and/or the second period of time) for only one time interval instead of consecutive time intervals). In another example, determination of an ESD event may be made when the persistent condition is not met (e.g., when U/V is not proportional to X/Y for one or more intervals). The processor 214 may be further configured to indicate that the ESD event is different from a wakeup event, store records in the sensor electronics module 106 of one or more occurrences of such ESD events, and may further send a notification to an appropriate entity regarding such events.

Some embodiments also include an interrupt glitch filter that determines whether a waveform signal is valid. An interrupt glitch filter can be used in sensor electronics module 106, for example. A interrupt signal from a wake source (e.g., between potentiostat 210 and processor 214) can be a waveform signal used to wake sensor electronics module 106 from a storage mode or can be any other waveform signal used during operation of sensor electronics module 106 to cause processor 214 or other sensor electronic module 106 components to switch between different states of operation, such as between a low power state of operation (e.g., sleep mode) and a powered up state of operation or other routine.

An interrupt glitch signal, on the other hand, can be a transient signal inadvertently generated due to vibration of the sensor electronics module 106 or to other spurious causes. An interrupt glitch signal can cause false and inadvertent interrupts, which can place sensor electronics module 106 into an unusable state unless the sensor electronics module 106 is, for example, reset.

In some embodiments, a waveform signal comprises a relatively complex waveform so a valid waveform signal can be discerned from a single signal glitch. The complex waveform can be designed so that it is highly unlikely that a single signal glitch would be the same as a valid waveform signal.

Further, in some embodiments, processor 214 of sensor electronics module 106 wakes from a sleep state and enters an operational state to determine whether a received interrupt signal is valid. If not valid, the processor 214 returns to a sleep state. Entering the operational state can consume a significant amount of power, however. For example, entering the operational state may power up numerous clocks, etc. that consume power. Thus, entering the operational state each time an interrupt signal is received can consume a lot of power if numerous interrupt glitches are received.

In some embodiments, the processor 214 or other logic separates an interrupt filter routine from normal operation so that the processor 214 need not wake to the operational state until the filter logic determines whether or not a signal is a valid interrupt signal. Instead, the processor 214 or other electronic components enter an interrupt check routine state, which can consume less power than waking the processor to its operational state.

In one embodiment, an interrupt filter routine can execute logic, which can be implemented in the form of a state machine, configured to determine whether an interrupt signal is part of a valid waveform signal or whether it is an inadvertent glitch. If the filter routine logic determines the entire waveform signal is valid, then—and only then—is the processor 214 of the sensor electronics module 106 allowed to discontinue its current mode of operation (e.g., exit a low power mode).

As discussed above, a valid waveform signal can be designed as a complex waveform. Upon receipt of each signal, the interrupt logic iteratively tests sections of the waveform to determine whether each section is valid. That is, the interrupt logic tests a first section of the waveform to confirm that the first section is the same as a first section of a valid waveform, followed by a second section, and so on, until the entire waveform is analyzed. If, however, any section is determined to be different from a valid waveform, then the interrupt routine determines that the single signal is not valid (e.g., an interrupt glitch), stops analyzing any further sections of the waveform signal and resets a state machine. If, on the other hand, the entire waveform is tested and each section is determined to be valid, then the interrupt routine determines that the waveform signal is valid and initiates a sensor electronics module 106 wake up routine.

In one embodiment, a state machine performs a plurality of iterative tests (such as 2, 5, 10, 20 or more) on each individual signal to determine if the entire waveform of the signal follows a valid predefined waveform. If, after the completion of any one of the plurality of tests, the state machine determines that the waveform is not valid, then the state machine resets and the state machine waits for the next individual waveform signal. In this manner, the state machine need not analyze a complete waveform signal to determine whether or not it is faulty. An iterative approach, such as the approach discussed above, can save power by quickly determining if a waveform signal is faulty and ending the process should one of the earlier sections being tested confirm that the signal is faulty—as opposed to analyzing the entire waveform signal regardless of whether earlier sections of the waveform signal are faulty.

Watchdog Reset

Various embodiments described above can address scenarios to conserve battery power in the context of, e.g., sensor electronics module 106, being in a low power or storage mode. For example, and again referring back to FIG. 4, sensor electronics module 106 may enter low power or no power modes during certain periods of inactivity, e.g., $T_{Inactive}$ periods, e.g., in between wireless communication sessions. However, in a scenario where sensor electronics module 106 should wake up in order to receive and transmit sensor information, it would be problematic if sensor electronics module 106 failed to wake up.

Accordingly, some embodiments implement a mechanism to ensure that sensor electronics module 106 wakes up when warranted. In particular, some embodiments utilize a watchdog timer. A watchdog timer is a hardware feature for an electronic component or circuit that has a countdown timer. A watchdog timer can be used to detect system anomalies or malfunctions and recover from them. For example, if the countdown timer reaches 0, the chip will reset. Since the watchdog is hardware and not software controlled, software errors will not interfere with its operation. In implementations, where under normal operating conditions of the electronic circuit, the watchdog timer is periodically restarted to prevent it from "timing out." If, however, due to a fault or other error, the system fails to restart the watchdog timer, it will elapse and one or more corrective actions may be taken, such as resetting system circuitry.

In the context of sensor electronics module 106, one type of low power mode that sensor electronics module 106 may enter is a low power mode where all clocks are turned off. Conventional watchdog timers are unable to operate under such a condition because conventional watchdog timers typically rely on a clock to "pet" the watchdog timer (e.g., send a signal to the watchdog timer to restart, also referred to as "kicking the dog"). In the event that a system is clockless, there is no element that can reset or restart the watchdog timer, and external circuitry is needed in order to detect whether or not a wake source has been sent to wake ASIC 205. Accordingly, a hardware or software error may put sensor electronics module 106 in an unrecoverable state.

To address the above scenario without the added complexity and requirement for additional, external circuitry/ system elements and requisite power to operate such external circuitry/system elements, some embodiments of the present technology utilize a low power oscillator, e.g., a very low power low-frequency oscillator (VLO) such as a 10 kHz oscillator in some embodiments, that allows a watchdog timer to be set and, upon elapsing, generate a signal to reset sensor electronics module 106 by way of ASIC 205. For example, if a wake source cannot wake up processor 214 or processor 214 cannot wake up transceiver 316, etc., the component requiring wake up can be reset.

The aforementioned VLO may be a resistor-capacitor (RC) oscillator used for, e.g., generic, very low current operations, which can be re-routed/have its registers reconfigured to send a signal to ASIC 205 to read counts (e.g., 9000 counts over a period of 5 minutes as described above in some embodiments) to allow processor 214 to determine whether or not to wake sensor electronics module 106 from a low power or no power mode. The VLO may also be configured to pet a watchdog timer that sensor electronics module 106 can revert to a low power or no power mode if processor 214 does not detect the requisite counts. Thus, the implementation of watchdog circuitry with the VLO enables various embodiments to remain power efficient while also provide increased user/patient safety.

Conductive Material on Transmitter Packaging

In some implementations, specific packaging materials (e.g., conductive materials) may be used in the packaging of the transmitter to facilitate operations of various modes of the transmitter. For example, start-up or wake-up mode of the transmitter or sensor electronics module 106 may be initiated, and/or the sleep mode may be maintained via the use of specific packaging materials.

Typically, during shipping and storage of the sensor electronics module 106, sleep mode may be maintained through use of non-conductive packaging materials, which protect the metal contacts from coming into contact with any potentially conductive materials. In one example, in order to initiate start-up of the transmitter and as described herein, to bring the transmitter out of the sleep mode and into active mode, the two metal contacts (e.g., contacts 244) on the underside of the transmitter unit may be simultaneously put into contact with an electrically conductive material. This action may then create a closed loop circuit through which the transmitter test current will flow, thus triggering a start-up sequence.

However, in some scenarios, upon receipt of a new sensor electronics module 106, a user may not be able to detect possible issues with the sensor electronics module 106 until after they have already inserted the transmitter into the sensor housing or mounting unit 240. Once the patient determines that the transmitter is not functioning as expected, the patient will have to remove the entire housing/ transmitter assembly, and redeploy once a new transmitter 106 and sensor 108 are available.

In order to circumvent such issues, in some implementations, the transmitter may be placed initially against a conductive material (e.g., a user may do so upon being provided with instruction). The placement may initiate a start-up sequence, allowing the user to verify functionality before inserting the transmitter into the mounting unit 240. In these implementations, the conductive material could be included in/on the package, for example, in the form of an adhesive label, or a label printed with conductive ink, in a selected area. The transmitter may be touched/placed/held against the conductive material for a predetermined amount of time, during which the transmitter would be awakened. It is contemplated that, upon initiation of the transmitter start-up mode, in some implementations, the conductive material or any other appropriate entity on the packaging, for example, may change color or cause a symbol to appear on the packaging.

Monitoring and Managing Battery Life

Referring back to FIGS. 2A and 3, sensor electronics module 106 operates under power provided by battery 234. If battery 234's power level is depleted, the analyte sensor system 104 may not be able to perform one or more functions and will eventually stop functioning altogether. For example, as the power level of battery 234 falls below a certain threshold amount, analyte sensor system 104 may not be able to transmit sensor information using transceiver 316 because the output voltage of battery 234 would be pulled below a threshold operation voltage of the transceiver 316 at a load current required for the transmission. At some intermediate level, it may be possible for the transceiver 316 to perform regularly-scheduled transmissions of analyte values but not bulk-transfers of stored, past analyte values. This is because the bulk transfer operation typically makes use of a special transmission mode of the transceiver 316 that draws a higher amount of current and/or requires a higher voltage as compared to a transmission mode used for regularly-scheduled transmissions. One conventional method of avoiding this issue is to disable sensor electronics module 106 after a predetermined amount of time, e.g., after 100 days. However, a myriad of circumstances (some discussed herein) as well as unpredictable factors, such as a defective cell, can deplete battery life sooner than its predicted/expected lifetime.

It is therefore desirable to monitor the current power level of battery 234 and predict when the life of battery 234 will end so that the amount (time) left for continued use of analyte sensor system 104 can be determined. By being cognizant of the current power level of battery 234, for example, it is possible to predict remaining useful life of battery 234 based on current power level and assumed future usage of the analyte sensor system 104. The analyte sensor system 104 may transmit data indicating the current power level and/or the predicted remaining useful life to one or more of display devices 120*a*-*e* that such information can be displayed to the user. In addition, it is possible to disable one or more functions of the analyte sensor system 8 when the current power level falls below a predetermined threshold power level and/or the predicted remaining useful life becomes less than a predetermined threshold time. In addition, the analyte sensor system 8 may transmit alerts to the one or more display devices 120*a-e* indicating such low battery conditions exist.

Figure 6A:
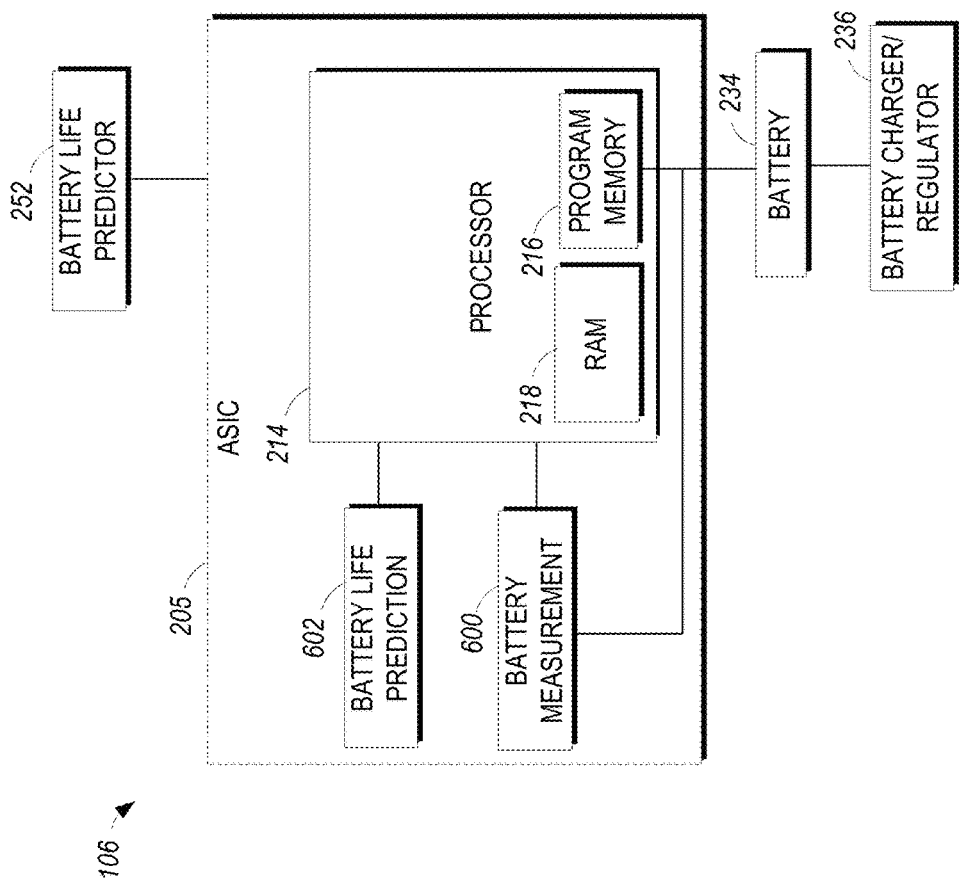
FIG. 6A is a block diagram illustrating a battery measurement and life prediction feature of the example sensor electronics module of FIG. 2A

FIG. 6A is an example block diagram of certain embodiments of certain components of sensor electronics module 106 capable of monitoring a current power level of a battery 234 installed in sensor electronics module 106 and predicting or determining remaining useful life of the battery 234. It should be noted that some components previously described and illustrated as being part of sensor electronics module 106 have been removed for ease of illustration and understanding.

In accordance with some embodiments, sensor electronics module 106 may include a battery measurement module 600 coupled to battery 234. Battery measurement module 600 may measure a value indicative of a current power level of the battery 234 and provide that measured value to processor 214, e.g., a data transmission control aspect or module therein (not shown), as well as to a battery life prediction module 602. Battery life prediction module 602 is configured for predicting remaining useful life of battery 234 based on the measured value indicative of a current power level of the battery 234 and assumed and/or a predetermined future usage of the analyte sensor system 104. The assumed future usage can be determined based on historical information regarding past usage (e.g., average and peak current levels and frequencies of regularly-scheduled transmissions and bulk transfers) stored in data storage memory 220 (FIG. 2A) and/or program memory 216. Based on such data, battery life prediction module 602 can calculate the expected frequencies of different types of transmission events and use the calculated frequencies as the basis for determining the assumed future usage. In certain embodiments, processor 214 controls one or more data transmission functions of sensor electronics module 106 based on the measured value indicative of the current power level of battery 234 and/or the predicted remaining useful life of battery 234.

Figure 6B:
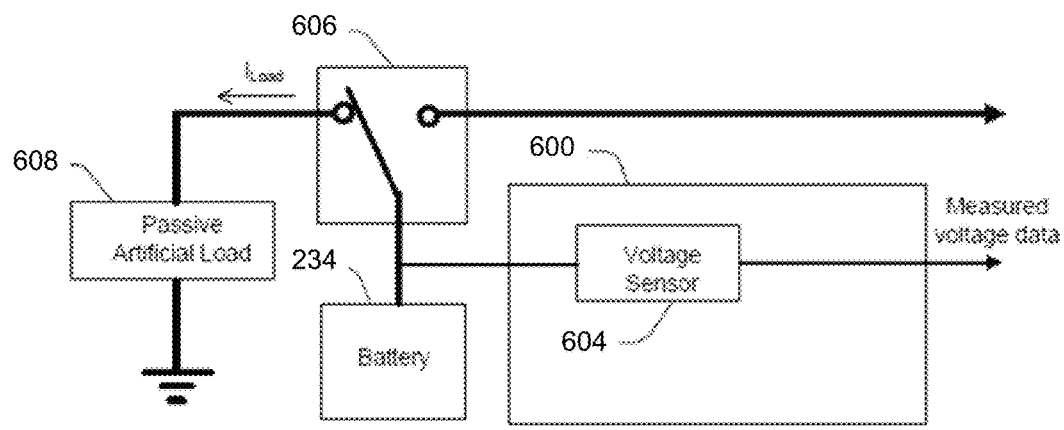
FIGS. 6B-6E are block diagrams of example implementations of battery measurement in accordance with various embodiments described in the present disclosure.
Figure 6C:
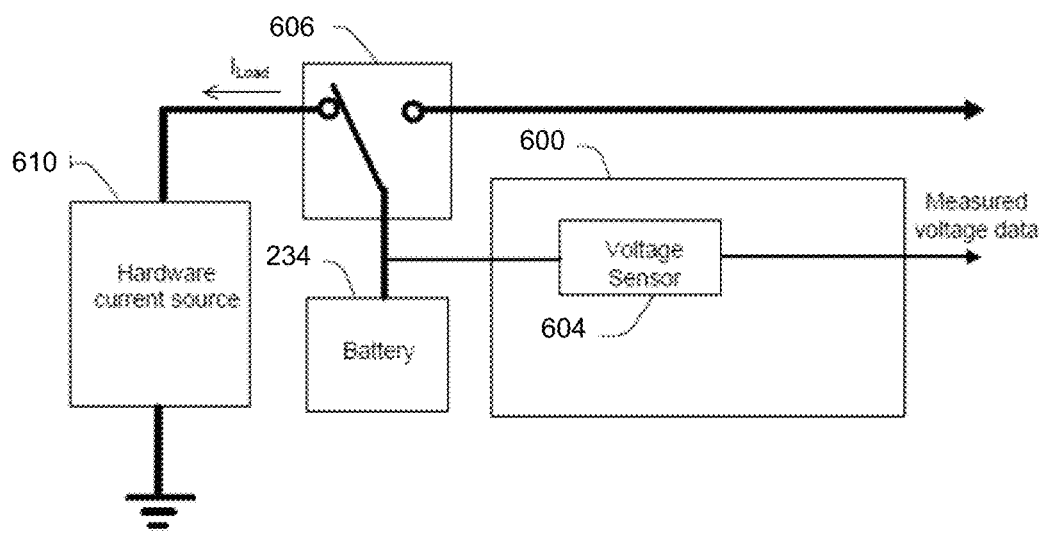
Figure 6D:
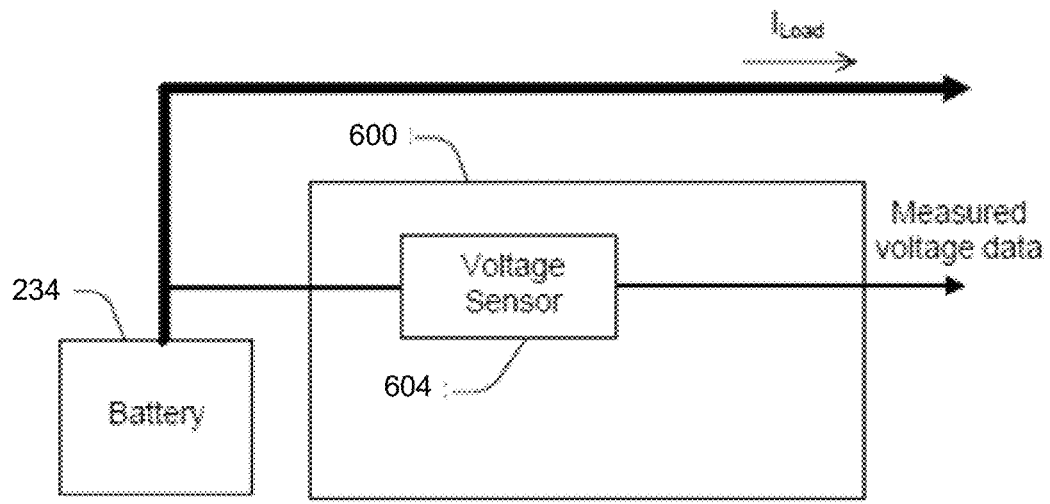

There are many different ways to implement battery measurement module 600 to measure the current power level of battery 234. With some batteries, the internal resistance increases as the battery's power level drops. Thus, the internal resistance can be a good indicator of the current power level of a battery. FIGS. 6B, 6C, and 6D are diagrams depicting three different example arrangements for implementing battery measurement module 600 configured to measure a voltage drop indicative of an internal resistance of battery 234 according to certain aspects of the present disclosure. In all three arrangements, battery measurement module 600 includes a voltage sensor 604 (e.g., an A/D converter) configured to measure a voltage drop at the battery 234.

In order to determine the internal resistance and current power level of battery 234, the voltage drop while the battery 234 is connected to a load that draws a known current is measured. In the embodiments illustrated in FIGS. 6B and 6C, battery 234 is disconnected from the actual load (i.e., the components of the sensor electronics module 106) via a switch 606 and is instead connected to an artificial load (608 in FIG. 6B and 610 in FIG. 6C), with known impedance or current-drawing characteristics. In FIG. 6B, for example, the artificial load 608 is a passive artificial load comprising passive electrical components such as a capacitor and/or a resistor. Because the impedance of the artificial load 608 is known, it is possible to determine the internal resistance of the battery 234 by monitoring the current flowing into the artificial load 608 as a function of time. In FIG. 6B, the artificial load 610 is an active artificial load or hardware comprising active components such as an operational amplifier or a MOSFET configured as a constant current source.

In FIG. 6D, the illustrated embodiment includes voltage sensor 604 in the battery measurement module 600, which measures a voltage drop while analyte sensor system 104 performs one or more tasks known to draw a constant current from the battery 234. Such tasks can include a specific wireless transmission mode. For example, in analyte sensor systems employing an ANT radio protocol, a transmission mode known as "ANT-FS" mode is known to draw a constant current from the battery. The ANT-FS mode may be used for a bulk transfer of data items stored in a database and, in analyte sensor systems employing the ANT radio protocol, the ANF-FS mode is typically used for a bulk transfer of stored past analyte values. In the embodiment of FIG. 6D, the battery measurement module 600 can be configured to measure the voltage drop at the battery 234 while the transceiver 316 is engaged in a specific wireless transmission mode (e.g., the ANT-FS mode) known to draw a constant current from the battery 234. In some embodiments, the voltage drop measurement can be made while the transceiver 316 is engaged a "fake" ANT-FS mode whereby the transceiver transmits "dummy" data such as all 0's or all 1's. After determining the voltage drop, the current power level of the battery 234 can be determined using one of a variety of methods known in the art. In some embodiments, a predetermined voltage profile curve associated with the battery 234 is stored in a memory (e.g., data storage memory 220 or program memory 216) and the current power level is determined by comparing the measured voltage drop to the stored, predetermined voltage profile curve. In one example, upon the comparison, when a profile of the measured voltage drop does not match with the stored predetermined voltage profile curve (e.g., when the measured voltage drop profile is above or below the stored voltage profile curve), the battery measurement module 600 may indicate to the battery life prediction module 602 and/or to the processor that the battery 234 does not meet the required life expectancy to operate the sensor electronics module 106.

Figure 6E:
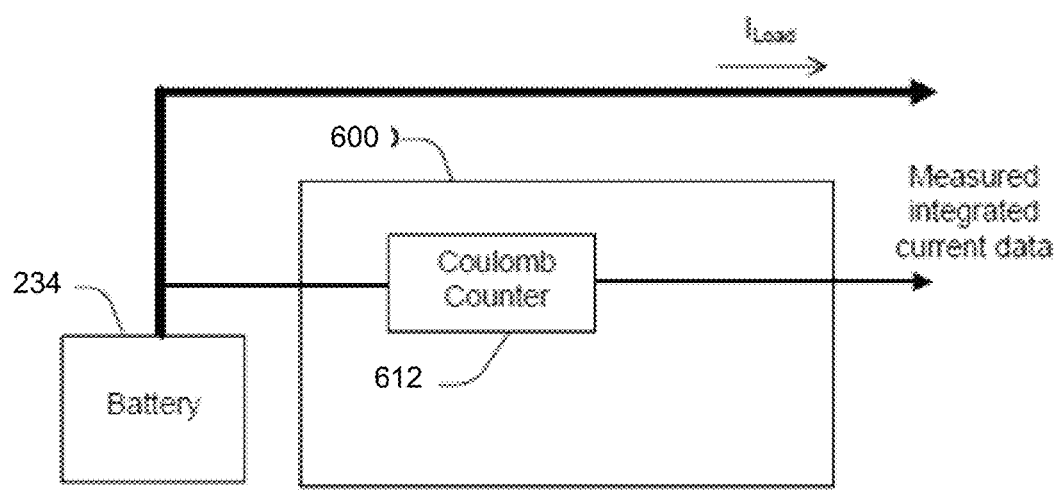

FIG. 6E is a diagram depicting an example arrangement in which the battery measurement module 600 includes a Coulomb counter 612. The Coulomb counter 612 is a device configured to provide a value indicative of an accumulated amount of charges drawn from the battery 234 or an integral of a load current drawn from the battery 234 over time. Knowledge of the accumulated amount of charges drawn from the battery 234 can be used to determine the current power level (e.g., state of charge) of the battery 234.

Figure 7:
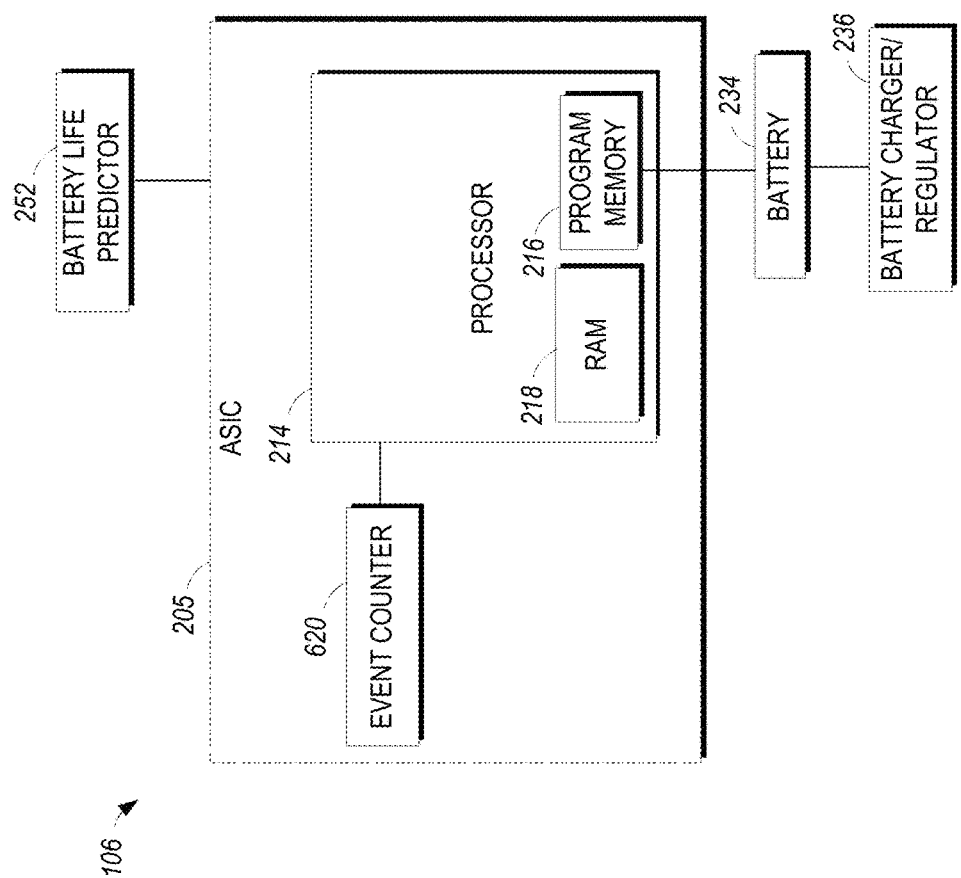
FIG. 7 is a block diagram illustrating a battery measurement and life prediction feature based on event counting in accordance with various embodiments described in the present disclosure.

The embodiments illustrated in FIGS. 6B-E include a battery measurement module to measure a certain parameter/characteristic of battery 234 such as voltage drop or load current. In some cases, however, the current power level of battery 234 can be determined by counting a number of specific events associated with usage of analyte sensor system 104. FIG. 7 is an example block diagram of certain embodiments of sensor electronics module 106 capable of monitoring a current power level of battery 234 and/or predicting the remaining useful life of battery 234 based on counting specific events associated with the usage of analyte sensor system 104 according to certain aspects of the present disclosure. It should be noted that usage of the analyte sensor system 104 may include usage of the entire analyte sensor system 104, e.g., when all the components thereof are active/in an operational mode, or may include when only one or some components, e.g., transceiver 316 or processor 214, are active/in an operational mode.

In the embodiment of FIG. 7, an event counter 620 is implemented in sensor electronics module 106 to count a number of events associated with usage of analyte sensor system 104. In some embodiments, the event counter 620 can be incremented commensurate with the number of events that occur based, e.g., on the type of transactions performed by analyte sensor system 104. For example, different transactions may be assigned different increment numbers commensurate with the power drawn from battery 234 to complete the transactions. By way of illustration, each regularly-scheduled transmission of an analyte value may be assigned an increment number of 1 while each bulk-transfer of stored past analyte values may be assigned an increment number of 10. Processor 214 can send a signal indicating the occurrence and type of each transaction and the event counter 620 can be incremented based on the type of each transaction. As such, event counter 620 provides an output that is indicative of a total amount of power drawn from the battery 234 thus far, and is therefore representative of a current (remaining) power level of the battery 234.

In some embodiments, the event counter 620 can be incremented based upon the number of events that have occurred since the battery 234 was first installed in sensor electronics module 106, including both when sensor electronics module 106 is in a low-power shelf (or storage) mode as well in normal operational mode. Thus, even if sensor electronics module 106 was sitting on a shelf before first usage, the event counter 620 can be configured to be incremented, at predetermined time intervals associated with the time it is in storage mode. This time-based incrementing scheme takes into account that even while it is inside a package on the shelf, sensor electronics module 106 is using power from the battery 234 for tasks such as checking an electrical contact to determine whether it has been removed from its packaging, periodic checking for counts, etc. It should be noted that although these types of tasks/occurrences, alone, may result in a very small power drain on battery 234, over time, their cumulative impact can be large. The time-based increment scheme can, therefore, provide a more accurate accounting of a current power level of the battery 234. In some examples, processor 214 may determine whether each event is utilizing or drawing an appropriate amount of power to perform the respective task associated with the event. In such examples, the processor 214 may consult event counter 620, and memory 218 and/or 216—which may store information related to the required amount of power for respective events. Processor may further compare the information stored in the memory 218 and/or 216 to determine whether a task has drawn appropriate power to carry out the task. In one example, when the processor determines that a discrepancy has occurred (e.g., an event has drawn more power than what is required), processor 214 may provide an indication to an appropriate entity. For example, a flag may be set in the ASIC 205 to indicate such discrepancies. In another example, processor 214 may or may not provide any indication when an event draws the appropriate power. It should be noted that other examples of battery life prediction and current battery power level measurement are disclosed in U.S. patent application Ser. No. 14/569,512, filed on Dec. 12, 2014, which is incorporated herein by reference in its entirety.

As described above, remaining battery life can be measured and/or predicted in accordance with various embodiments. However, certain conditions may arise that affect the measurement(s) and/or predictions associated with battery life resulting in false measurements and/or false predictions of battery life. For example, the temperature of sensor electronics module 106 and/or host 102 can skew the current power level of battery 234. To counteract this potential effect on battery life measurements and predictions, various embodiments may determine the temperature of sensor electronics module 106 and/or host 102 in relation to performance characteristics of battery 234 and maintained in, e.g., a temperature-battery power skew table or implemented in a temperature-battery power skew algorithm/equation-based correction scheme. Such temperature readings can be taken into account when determining the current power level and predicted life of battery 234. In particular, a temperature sensor, e.g., temperature sensor 252 (FIG. 2A), can be used to gauge the temperature of host 102 and/or sensor electronics module 106. For example, colder than normal temperatures may increase the internal resistance of battery 234, thereby lowering its capacity but increasing its life, while the converse is true of hotter than normal operating temperatures. Accordingly, temperature sensor 252 can be used to measure the ambient temperature about battery 234 (which can be host 102 and/or sensor electronics module 106). Based on this temperature measurement, the current power level and predicted battery life of battery 234 can be appropriately adjusted to compensate for the temperature in which battery 234 is operating. That is, upon performing a temperature measurement, the aforementioned table or algorithm/equation-based correction scheme can be accessed, and the predicted life/remaining energy of battery 234 can be shifted. For example, testing of batteries may suggest that at a temperature of 10 degrees Fahrenheit, battery 234 (or batteries of the same type as battery 234) may tend to measure at a low power, despite having additional power to emit. In this instance, the predicted life/energy of battery 234 can be shifted based on this observed characteristic that is captured in the aforementioned table or determinable via the aforementioned algorithm/equation-based correction scheme.

Figure 8A:
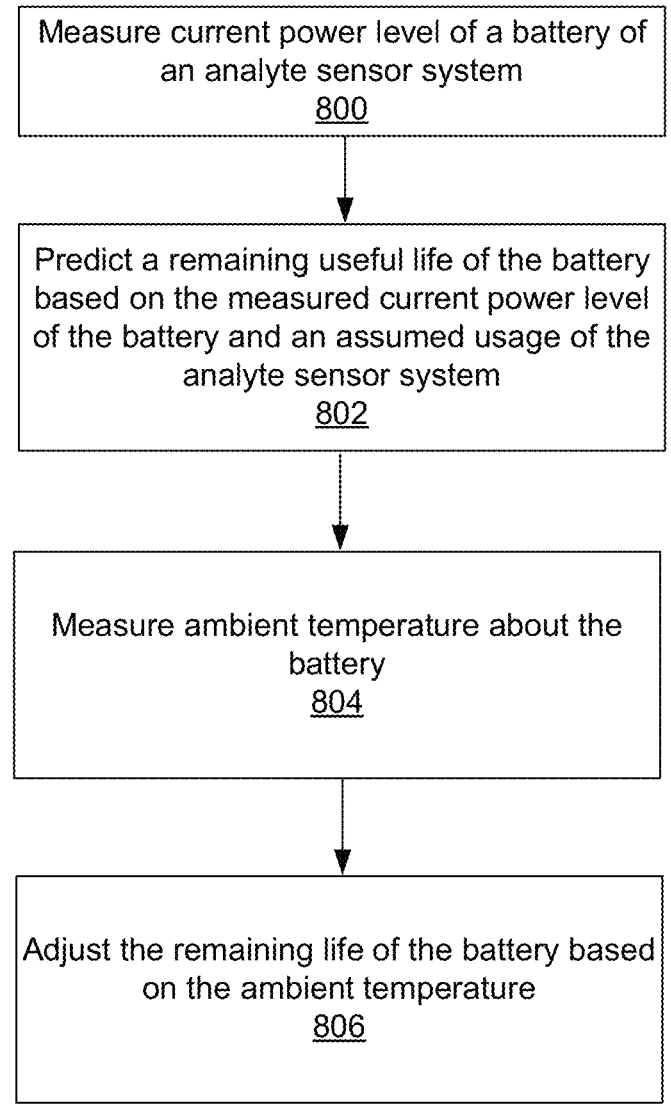
FIG. 8A is a flow chart illustrating example operations performed for compensating predicted battery life predictions based on temperature.

FIG. 8A is a flow chart illustrating example operations performed to compensate for temperature when measuring battery power level and predicting battery life. At operation 800, a current power level of a battery (e.g., battery 234) of an analyte sensor system (e.g., analyte sensor system 104) is measured. As described above, the measurement of the current power level of battery 234 can be accomplished using a variety of methods/systems, such as using by measuring voltage drop and comparing it to a stored voltage profile curve. Other ways to measure the current power level of battery 234 can rely on event counting. At operation 802, a remaining useful life of the battery is predicted based on the measured current power level of the battery and an assumed usage of the analyte sensor system. As also described above, assumed usage of analyte sensor system 104 can be based on historical information regarding past usage (e.g., average and peak current levels and frequencies of regularly-scheduled transmissions and bulk transfers). At operation 804, ambient temperature about the battery is measured. For example, the temperature of host 102 and/or the temperature of sensor electronics module 106 can be measured. At operation 806, the remaining useful life of the battery is adjusted based on the ambient temperature.

Depending on the current power level of battery 234 and/or its predicted remaining lifetime, various actions can be undertaken commensurate with that current power level/predicted remaining lifetime. For example, if the current power level reaches or falls below a certain predetermined power level, sensor electronics module 106 may send one or more warnings or notifications to be displayed on one or more of display devices 120a-e. Furthermore, minimizing battery drain can also be considered by, e.g., performing or not performing certain operations, such as delaying or preventing subsequent analyte measurements. Moreover, current power levels/predicted remaining lifetime can be used as progressive bases for the performance or non-performance of operations. For example, when battery 234 reaches a first power level, one of the aforementioned notifications may be sent, and when battery 234 reaches a second power level (e.g., a power level that is lower than the first power level), analyte measurement is prohibited and/or sensor electronics module 106 may be shut down.

Still other actions may be performed or prohibited, where the other actions are associated with the initiation of and/or communication with one or more of display devices 120a-e. That is, two-way communications between sensor electronics module 106 and one or more of display devices 120a-e can be disabled in favor of one-way communications, where sensor information is embedded or appended to advertising messages or beacons. The transmission power used by transceiver 316 can be lessened or progressively ratcheted down as the power level of battery 234 decreases. Yet another example may be to operate in an on-demand (e.g., NFC-based) transmission scheme instead of an automatic transmission scheme. Further still, advertising durations and/or intervals may be adjusted, the order of or allowed connections to one or more of display devices 120a-e may be altered (based on display device type, last successful connection or likelihood of connection, etc.) In some embodiments, one or more of display devices 120a-e may be transitioned from acting as a receiver of sensor data to being an advertising and/or sensor information-forwarding display device.

Figure 8B:
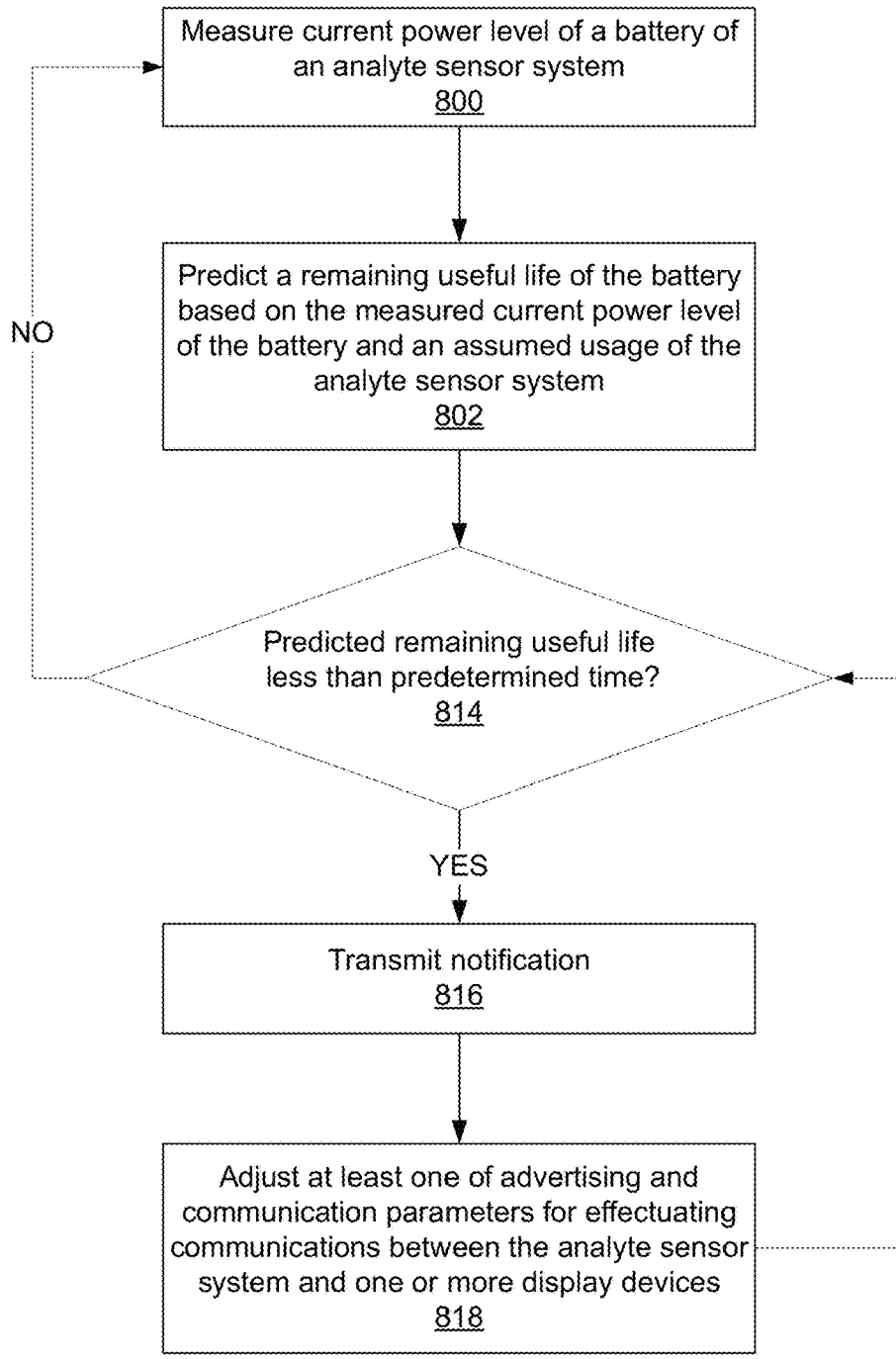
FIG. 8B is a flow chart illustrating example operations performed for adjusting advertising and/or communication parameters based upon battery life predictions in accordance with various embodiments described in the present disclosure.

FIG. 8B is a flow chart illustrating example operations performed for adjusting one or more advertising and/or communications parameters based on a battery's predicted lifetime. At operation 800, a current power level of a battery (e.g., battery 234) of an analyte sensor system (e.g., analyte sensor system 104) is measured. As described above, the measurement of the current power level of battery 234 can be accomplished using a variety of methods/systems, such as using by measuring voltage drop and comparing it to a stored voltage profile curve. Other ways to measure the current power level of battery 234 can rely on event counting. At operation 802, a remaining useful life of the battery is predicted based on the measured current power level of the battery and an assumed usage of the analyte sensor system. At operation 814, it is determined whether the predicted remaining useful life of the battery is less than a predetermined time. The predetermined time can be set based upon known operational limits of analyte sensor system 104, characteristics of battery 234, etc. The predetermined time can be preset upon configuring/manufacturing sensor electronics module 106 or can be determined dynamically based, e.g., on the aforementioned assumed usage of analyte sensor system 104. If the predicted remaining useful life of battery 234 is less than the predetermined time, a notification is transmitted at operation 816, but if not, the operations for measuring current power level and remaining useful life prediction can be repeated at some predefined interval. The notification transmission can be to one or more of display devices 120a-e and/or can simply be activating a warning light, such as a LED on sensor electronics module 106 or some other component(s) of analyte sensor system 104, such as mounting unit 240. At operation 818, at least one of advertising and communication parameters/variables for effectuating communications between analyte sensor system 104 and one or more of display devices 120a-e is adjusted.

In still other embodiments, sensor information can be taken into consideration as well. For example, if it is determined that a current trend of analyte measurements indicates that host 102 is in a "safe" condition, processor 214 can delay or increase the time between sensor information transmission by transceiver 316. If however, it is determined that a current trend of analyte measurements indicates that host 102 may be progressing towards a "critical" condition, alarms may be sent one or more display devices 120a-e indicating that a replacement battery or replacement sensor electronics module is needed as soon as possible and/or as described above, one or more of display devices 120a-e may take on the role of advertising or sensor information forwarding so as to preserve what battery life remains in battery 234. Examples of advertising and communication variables and conditions that may be adjusted in accordance with various embodiments can be found in U.S. Provisional Patent Application No. 62/106,150, which is incorporated herein by reference in its entirety. It should be noted that the examples described herein are not meant to be limiting and other embodiments are contemplated.

It should also be noted that various combinations of the above-mentioned embodiments/operational scenarios can be combined in different ways to achieve one or more desired operational characteristics in a continuous analyte measurement system. Although various embodiments have been described in the context of continuous analyte measurement, e.g., continuous glucose monitoring, the various embodiments can be adapted for use in other context as well, e.g., for monitoring vital signals.

Figure 9:
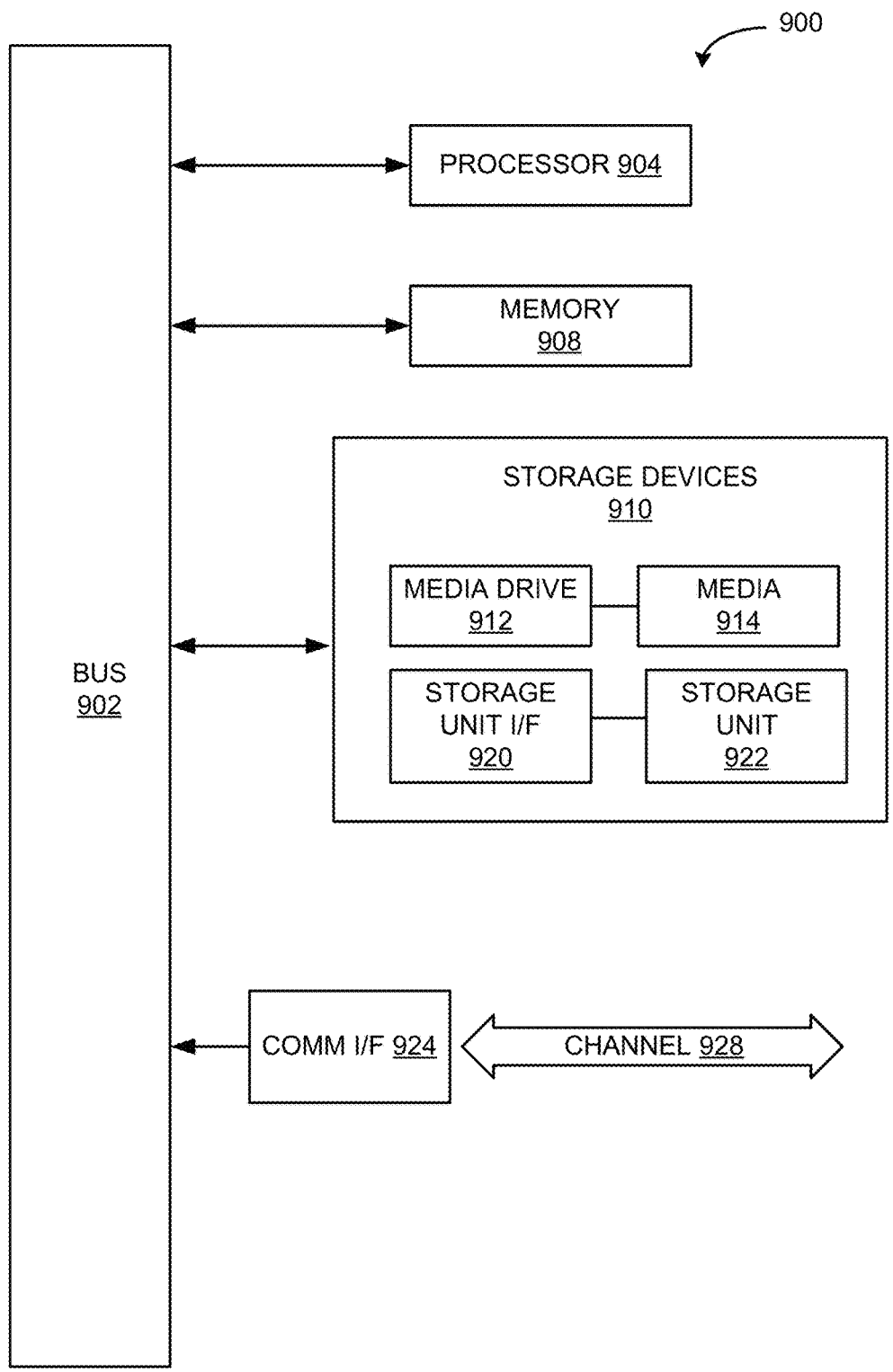
FIG. 9 is a block diagram of an example computing module that may be used to implement various features of embodiments described in the present disclosure.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. The modules, circuitry, processors, etc. may be affixed to a printed circuit board (PCB), or the like, and may take a variety of forms. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 9 which may be used to implement various features of the system and methods disclosed herein. Various embodiments are described in terms of this example computing module 900. After reading this description, it will become apparent to a person skilled in the relevant art how to implement the application using other computing modules or architectures.

Referring now to FIG. 9, computing module 900 may represent, for example, computing or processing capabilities found within a self-adjusting display, desktop, laptop, notebook, and tablet computers; hand-held computing devices (tablets, PDA's, smart phones, cell phones, palmtops, etc.); workstations or other devices with displays; servers; or any other type of special-purpose or general-purpose computing devices as may be desirable or appropriate for a given application or environment. For example, computing module 900 may be one embodiment of one of display devices 120a-e, sensor electronics module 106, etc. Computing module 900 might also represent computing capabilities embedded within or otherwise available to a given device. For example, a computing module might be found in other electronic devices such as, for example, portable computing devices, and other electronic devices that might include some form of processing capability.

Computing module 900 might include, for example, one or more processors, controllers, control modules, or other processing devices, such as a processor 904. Processor 904 might be implemented using a general-purpose or special-purpose processing engine such as, for example, a microprocessor, controller, or other control logic. In the illustrated example, processor 904 is connected to a bus 902, although any communication medium can be used to facilitate interaction with other components of computing module 900 or to communicate externally.

Computing module 900 might also include one or more memory modules, simply referred to herein as main memory 908. For example, preferably random access memory (RAM) or other dynamic memory might be used for storing information and instructions to be executed by processor 904. Main memory 908 might also be used for storing temporary variables or other intermediate information during execution of instructions to be executed by processor 904. Computing module 900 might likewise include a read only memory ("ROM") or other static storage device coupled to bus 902 for storing static information and instructions for processor 904.

The computing module 900 might also include one or more various forms of information storage mechanism 910, which might include, for example, a media drive 912 and a storage unit interface 920. The media drive 912 might include a drive or other mechanism to support fixed or removable storage media 914. For example, a hard disk drive, a solid state drive, a magnetic tape drive, an optical disk drive, a compact disc (CD) or digital video disc (DVD) drive (R or RW), or other removable or fixed media drive might be provided. Accordingly, storage media 914 might include, for example, a hard disk, an integrated circuit assembly, magnetic tape, cartridge, optical disk, a CD or DVD, or other fixed or removable medium that is read by, written to or accessed by media drive 912. As these examples illustrate, the storage media 914 can include a computer usable storage medium having stored therein computer software or data.

In alternative embodiments, information storage mechanism 910 might include other similar instrumentalities for allowing computer programs or other instructions or data to be loaded into computing module 900. Such instrumentalities might include, for example, a fixed or removable storage unit 922 and an interface 920. Examples of such storage units 922 and interfaces 920 can include a program cartridge and cartridge interface, a removable memory (for example, a flash memory or other removable memory module) and memory slot, a PCMCIA slot and card, and other fixed or removable storage units 922 and interfaces 920 that allow software and data to be transferred from the storage unit 922 to computing module 900.

Computing module 900 might also include a communications interface 924. Communications interface 924 might be used to allow software and data to be transferred between computing module 900 and external devices. Examples of communications interface 924 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 924 might typically be carried on signals, which can be electronic, electromagnetic (which includes optical) or other signals capable of being exchanged by a given communications interface 924. These signals might be provided to communications interface 924 via a channel 928. This channel 928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 908, storage unit 920, media 914, and channel 928. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 900 to perform features or functions of the present application as discussed herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not 'limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the present disclosure, but instead as merely intended to highlight alternative or additional features that may or may not be utilized in a particular embodiment. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the present disclosure to the specific embodiments and examples described herein, but rather to also cover all modification and alternatives coming with the true scope and spirit of the present disclosure.

What is claimed is:

1. A computer-implemented method for estimating battery life, comprising:
    measuring a current power level of a battery powering an analyte sensor system;
    predicting a remaining useful life of the battery based upon the measured current power level of the battery and an assumed usage of the analyte sensor system;
    determining whether the predicted remaining useful life of the battery is less than a predetermined time;

adjusting at least one of advertising and communication parameters for effectuating communications between the analyte sensor system and one or more display devices; and delaying the communications between the analyte sensor system and the one or more display devices upon a determination that a current trend of analyte measurements received by the analyte sensor system is indicative that a user of the analyte sensor system is in a clinically safe zone.

2. The computer-implemented method of claim 1, further comprising transmitting a notification to at least one of the one or more display devices upon a determination that the predicted remaining useful life of the battery is less than the predetermined time.

3. A computer-implemented method for estimating battery life, comprising:

measuring a current power level of a battery powering an analyte sensor system;

predicting a remaining useful life of the battery based upon the measured current power level of the battery and an assumed usage of the analyte sensor system;

determining whether the predicted remaining useful life of the battery is less than a predetermined time;

adjusting at least one of advertising and communication parameters for effectuating communications between the analyte sensor system and one or more display devices; and at least one of transmitting an alarm indicating that the battery requires replacement upon a determination that a current trend of analyte measurements received by the analyte sensor system is indicative that a user of the analyte sensor system is in a clinically unsafe zone and upon a determination that the predicted remaining useful life of the battery is less than the predetermined time.

4. The computer-implemented method of claim 3, further comprising transmitting a notification to at least one of the one or more display devices upon a determination that the predicted remaining useful life of the battery is less than the predetermined time.

5. A computer-implemented method for estimating battery life, comprising:

measuring a current power level of a battery powering an analyte sensor system;

predicting a remaining useful life of the battery based upon the measured current power level of the battery and an assumed usage of the analyte sensor system;

determining whether the predicted remaining useful life of the battery is less than a predetermined time;

adjusting at least one of advertising and communication parameters for effectuating communications between the analyte sensor system and one or more display devices; and handing off at least one of advertising for communications between the analyte sensor system and the one or more display devices and forwarding of analyte sensor information to the one or more display devices upon a determination that a current trend of analyte measurements received by the analyte sensor system is indicative that a user of the analyte sensor system is in a clinically unsafe zone and upon a determination that the predicted remaining useful life of the battery is less than the predetermined time.

6. The computer-implemented method of claim 4, further comprising transmitting a notification to at least one of the one or more display devices upon a determination that the predicted remaining useful life of the battery is less than the predetermined time.

* * * * *

UNITED STATES PATENT AND TRADEMARK OFFICE
CERTIFICATE OF CORRECTION

PATENT NO. : 10,231,655 B2
APPLICATION NO. : 15/369610
DATED : March 19, 2019
INVENTOR(S) : Jeffrey R. Wedekind It is certified that error appears in the above-identified patent and that said Letters Patent is hereby corrected as shown below:

In the Specification

In Column 2 at Line 12, Change "The" to --the--.

In Column 4 at Line 18, Change "2A" to --2A.--.

In Column 4 at Line 26, Change "2A" to --2A.--.

In Column 8 at Line 38, Change "andrenostenedione;" to --androstenedione;--.

In Column 8 at Line 54, Change "diptheria/" to --diphtheria/--.

In Column 8 at Line 61, Change "perioxidase;" to --peroxidase;--.

In Column 9 at Lines 3-4, Change "sissomicin;" to --sisomicin;--.

In Column 9 at Line 8, Change "duodenalisa," to --duodenalis,--.

In Column 9 at Line 16, Change "Trepenoma pallidium," to --Treponema pallidum,--.

In Column 9 at Line 17, Change "stomatis" to --stomatitis--.

In Column 18 at Line 23, Change "No." to --Nos.--.

In Column 19 at Line 1, Change "disposed of" to --disposed off--.

In Column 36 at Line 15, Change "ANF-FS" to --ANT-FS--.

Signed and Sealed this
First Day of October, 2019

Andrei Iancu
*Director of the United States Patent and Trademark Office*

In Column 43 at Line 8, Change "including" to --'including--.

In Column 43 at Line 8, Change "'limited" to --limited--.